(12) United States Patent
Zhang

(10) Patent No.: US 6,521,769 B1
(45) Date of Patent: Feb. 18, 2003

(54) CHIRAL PHOSPHINES, TRANSITION METAL COMPLEXES THEREOF AND USES THEREOF IN ASYMMETRIC REACTIONS

(75) Inventor: Xumu Zhang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 99 days.

(21) Appl. No.: 09/665,456

(22) Filed: Sep. 19, 2000

Related U.S. Application Data

(60) Provisional application No. 60/154,845, filed on Sep. 20, 1999.

(51) Int. Cl.$^7$ .................................................. C07F 7/08
(52) U.S. Cl. .................. 556/19; 556/419; 556/479; 556/405; 556/1; 556/51; 556/45; 556/136; 556/137; 562/152; 562/155; 562/159; 562/162; 562/167; 540/179; 540/542; 540/544; 540/547; 540/548; 549/349; 549/232; 549/12; 549/16; 549/17
(58) Field of Search ..................... 556/479, 419, 556/19, 136, 137, 45, 51, 1, 405; 562/152, 155, 159, 162, 167; 549/349, 232, 12, 16, 17; 540/179, 542, 544, 547, 548

(56) References Cited

U.S. PATENT DOCUMENTS

| | | | |
|---|---|---|---|
| 5,624,128 A | 4/1997 | Jendralla | 556/18 |
| 5,847,222 A | 12/1998 | Yokozawa et al. | 568/16 |
| 5,880,301 A | 3/1999 | Shibasaki et al. | 556/21 |
| 5,907,045 A | 5/1999 | Antognazza et al. | 549/6 |

*Primary Examiner*—Paul F. Shaver
(74) *Attorney, Agent, or Firm*—Ohlandt, Greeley, Ruggiero & Perle, L.L.P.

(57) ABSTRACT

Chiral ligands and transition metal complexes based on such chiral ligands useful in asymmetric catalysis are disclosed. The chiral ligands include chiral C1–C6 TunaPhos ligands. The ruthenium TunaPhos complex reduces ketones to the corresponding alcohols with 95–99.6% enantioselectivity. The transition metal complexes of the chiral ligands are useful in asymmetric reactions such as asymmetric hydrogenation, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation reactions.

32 Claims, No Drawings

CHIRAL PHOSPHINES, TRANSITION METAL COMPLEXES THEREOF AND USES THEREOF IN ASYMMETRIC REACTIONS

This application claims priority from Provisional Applications Ser. No. 60/154,845 filed on Sep. 20, 1999.

BACKGROUND OF THE INVENTION

1. Field of the Invention

The present invention relates to novel chiral biaryl phosphines and chelating phosphines with tunable bite angles for applications in asymmetric catalysis. More particularly, the present invention relates to transition metal complexes of these ligands, which are useful as catalysts in asymmetric reactions.

2. Description of the Prior Art

Discovery of new chiral ligands is crucial in developing highly enantioselective transition metal-catalyzed reactions. Despite the large number of chiral ligands that have been made for applications in asymmetric catalysis, only few chiral ligands or synthetic routes or motifs have been commonly used in the synthesis of chiral molecules by the chemical industry or academic laboratories.

Among these ligands, BINAP is one of frequently used chiral ligands. The axially dissymmetric, fully aromatic BINAP have demonstrated to be highly effective for many asymmetric reactions (Noyori, R; Takaya, H. *Acc. Chem. Res.* 1990, 23, 345; Olkuma, T.; Koizumi, M.; Doucet, H.; Pham, T.; Kozawa, M.; Murata, K.; Katayama, E.; Yokozawa, T.; Ikariya, T.; Noyori, R *J. Am. Chem. Soc.* 1998, 120, 13529). Related axially dissymmetric ligands such as MeO-BIPHEP and BIPHEMP were made and used for a number of asymmetric reactions (Schmid, R. et al. *Pure & Appl. Chem.* 1996, 68, 131; Foricher, J.: Heiser, B.; Schmid, R. U.S. Pat. No. 5,302,738; Michel, L.; European Patent Application 0667350A1; Broger, E. A.; Foricher, J.; Heiser, B.; Schmid, R. PCT WO 92/16536). Several chiral biaryl phosphines known in the literature are depicted below.

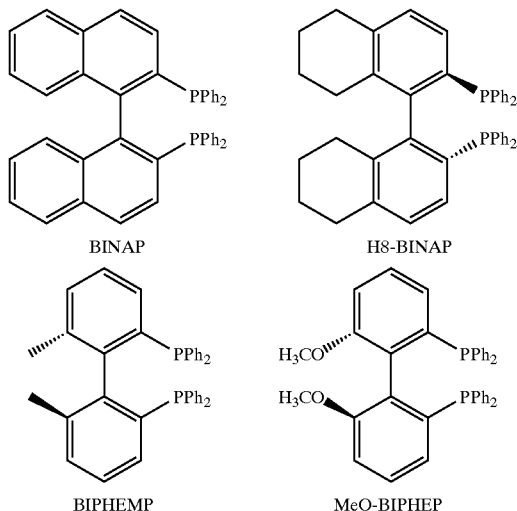

BINAP        H8-BINAP

BIPHEMP      MeO-BIPHEP

Despite the extensive research in this area, there are still a variety of reactions in which only modest enantioselectivity has been achieved with these ligands. Specially, the free rotation in certain degrees makes BINAP as a conformationally flexible ligand. Recent results suggest that partially hydrogenated BINAP with a bigger bite angle, i.e., H8-BINAP, may be a better ligand in certain asymmetric reactions.

For example, restricting conformational flexibility can enhance enantioselectivity (Uemura, T.; Zhang, X.; Matsumura, K.; Sayo, N.; Kumobayashi, H.; Ohta, T.; Nozaii, K.; Takaya, H. *J. Org Chem.* 1996, 61, 5510). For most chiral axially dissymmetric phosphine ligands, there is a low energy bite angle dictated by the metal species and a large degree of free rotation. The bite angle of chelating chiral phosphines is difficult to fine-tune. Change of ligand electronic properties can also contribute to the activity as well as to the enantioselectivity of a reaction. Because different substrates require different size of chiral pockets, it is important to have a tunable chiral ligand system to achieve high enantioselectivity.

The present invention includes tunable chiral biaryl phosphine ligands with a variety of bite angles by lining two aryl groups with a variety of bridges. Several new chiral biaryl phosphines are disclosed. To achieve heterogenous and supported catalysts, a number of approaches to ligand systems have been developed. These include linking these ligands to a polymer chain, organic or inorganic supports such as dendrimers, silica gel and molecular sieves. Water-soluble groups can be easily introduced into the ligands and fluorocarbon chains can be introduced to promote phase separation.

Catalysts derived from the ligands of the present invention are employed in a variety of asymmetric reactions such as hydrogenation, hydride transfer reaction, hydrosilylation, hydroboration, hydrovinylation, hydroformylation, hydrocarboxylation, isomerization, allylic alkylation, cyclopropanation, Diels-Alder reaction, Aldol reaction, Heck reaction and Michael addition to prepare asymmetric compounds having high enantiomeric purity.

SUMMARY OF THE INVENTION

The present invention includes a ligand selected from the group consisting of compounds represented by A through Z, AA, BB and CC:

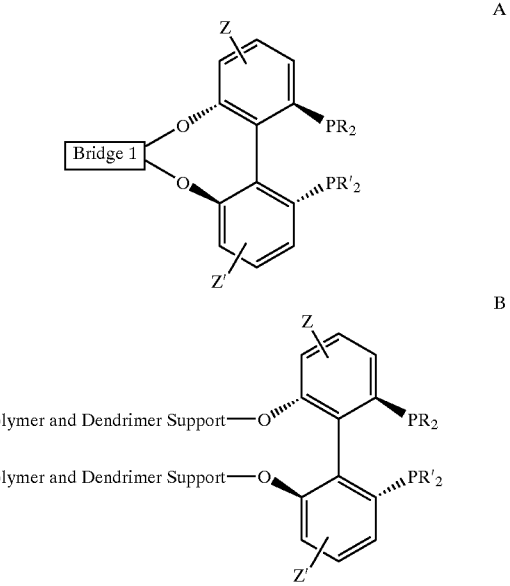

C
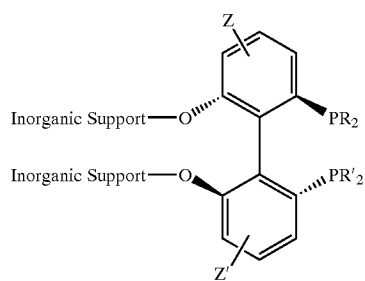
D
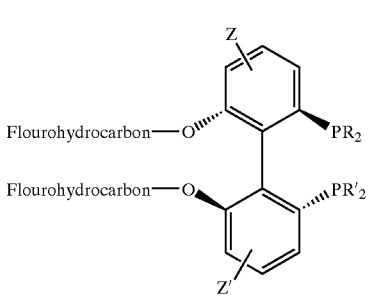
E
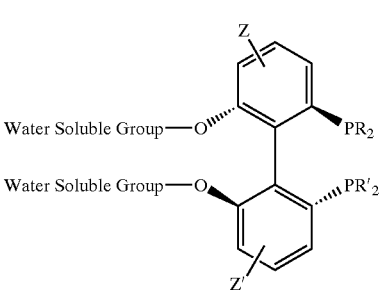
F
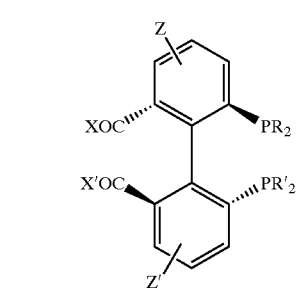
G
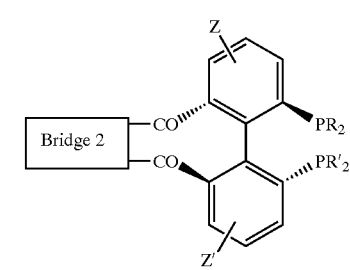
H
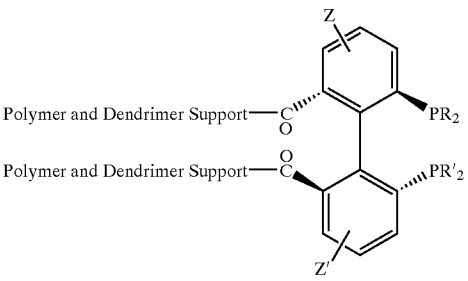
I
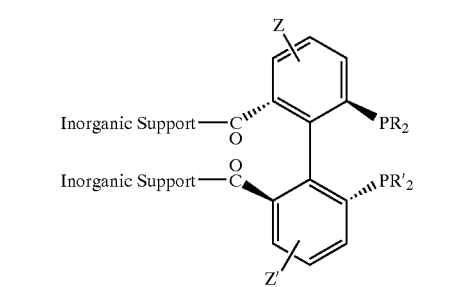
J
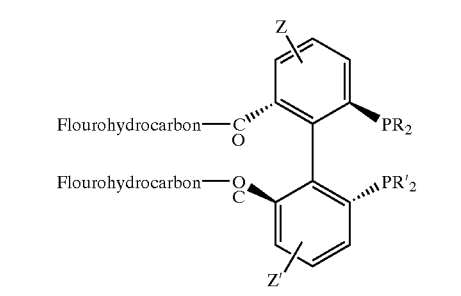
K
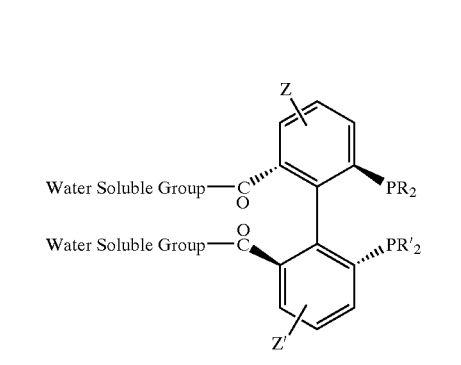
L
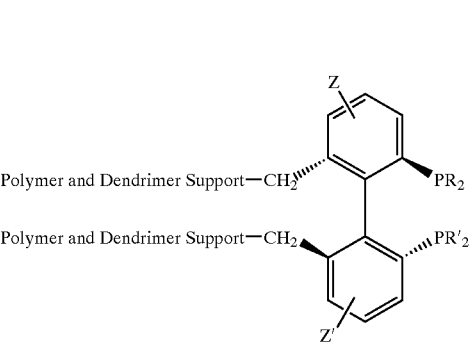

M
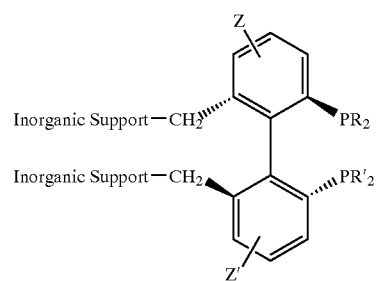
N
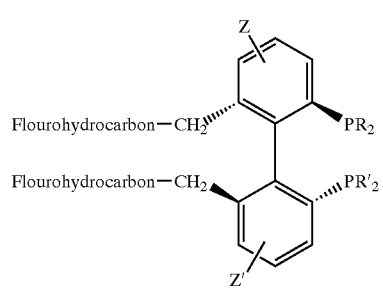
O
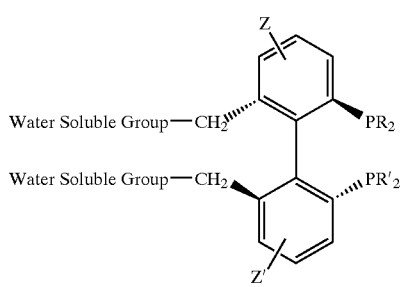
P
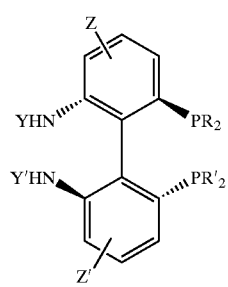
Q
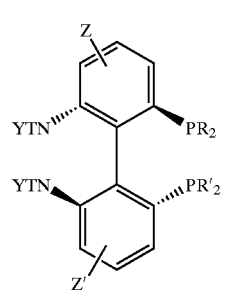
R
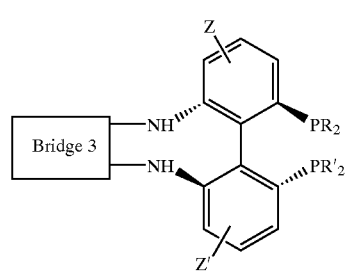
S
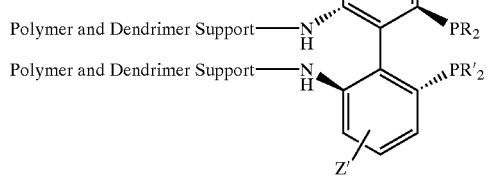
T
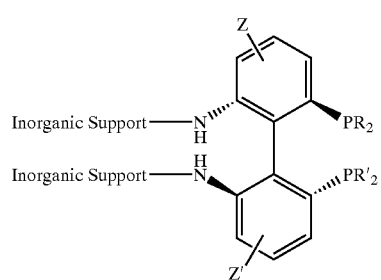
U
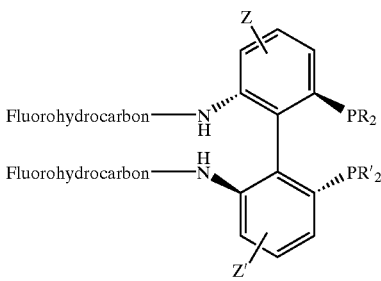
V
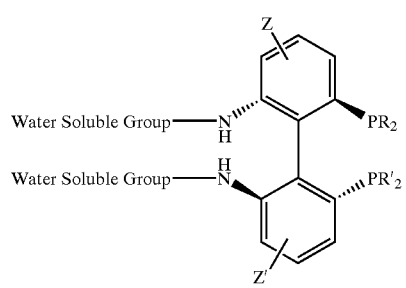

-continued

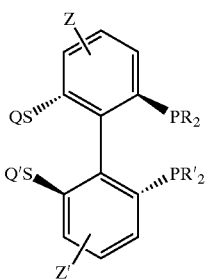
W

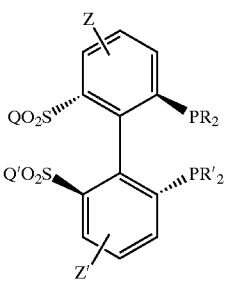
X

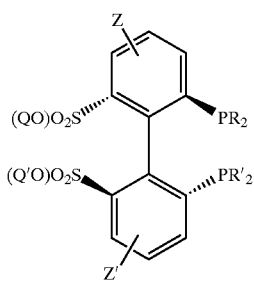
Y

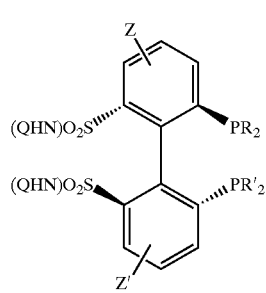
Z

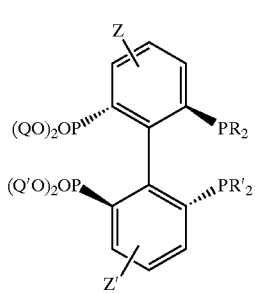
AA

-continued

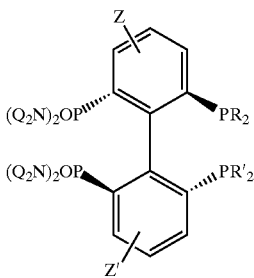
BB

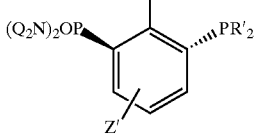
CC wherein "bridge 1" is selected from the group consisting of: C=O, C=S, SO$_2$, PO(OR$^1$), PO(NHR$^1$), PO(NR$^1$R$^2$), divalent phenyl, substituted divalent phenyl, 2,2'-divalent-1,1'-biphenyl, substituted 2,2'-divalent-1,1'-biphenyl, 2,2'-divalent-1,1'-binaphthyl, substituted 2,2'-divatent-1,1'-binaphthyl, 1,1'-ferrocene, substituted 1,1'-ferrocene, SiR$^1_2$ (CH$_2$)$_n$ where n is an integer ranging from 1 to 8, and (CR$^2_2$)$_n$X$^1$(CR$^2_2$)$_m$ wherein each n, m is independently an integer from 1 to 8, wherein X$^1$ is selected from the group consisting of O, S, NR$^3$, PR$^3_2$, $^+$NR$^3_2$, $^+$PR$^3_2$, divalent aryl, divalent fused aryl, divalent 5-membered ring heterocyclic group and divalent fused heterocyclic group;

wherein "bridge 2" is selected from the group consisting of: NH, O, a single bond, (CH$_2$)$_n$, O(CH$_2$)$_n$O, NH(CH$_2$)$_n$ NKn wherein each n is independently an integer from 1 to 8, divalent phenyl, substituted divalent phenyl, divalent phenyl amine, substituted divalent phenyl amine, 2,2'-divalent-1,1'-biphenyl, substituted 2,2'-divalent-1,1'-biphenyl, 2,2'-divalent-1,1'-binaphthyl, substituted 2,2'-divalent-1,1'-binaphthyl, 1,1'-ferrocene, substituted 1,1'-ferrocene, O(CR$^2_2$)$_n$X$^1$(CR$^2_2$)$_m$O, NH(CR$^2_2$)$_n$X$^1$(CR$^2_2$)$_m$NH and (CR$^2_2$)$_n$X$^1$(CR$^2_2$)$_m$ wherein each n, m is independently an integer from 1 to 8, wherein X$^1$ is selected from the group consisting of: O, S, NR$^3$, PR$^3_2$, $^+$NR$^3_2$, $^+$PR$^3_2$, divalent aryl, divalent fused aryl, divalent 5-membered ring heterocyclic group and divalent fused heterocyclic group;

wherein "bridge 3" is selected from the group consisting of: SO$_2$, CO, COCO, OC(CH$_2$)$_n$CO, (CH$_2$)$_n$ wherein n is an integer ranging from 1 to 8, COArCO, wherein Ar is selected from the group consisting of: divalent phenyl, substituted divalent phenyl, 2,2'-divalent-1,1'-biphenyl, substituted 2,2'-divalent-1,1'-biphenyl, 2,2'-divalent-1,1'-binaphthyl, substituted 2,2'-divalent-1,1'-binaphthyl, 1,1'-ferrocene, substituted 1,1'-ferrocene and CO(CR$^2_2$)$_n$X$^1$(CR$^2_2$)$_m$CO wherein each n, m is independently an integer from 1 to 8, wherein X$^1$ is selected from the group consisting of: O, S, NR$^3$, PR$^3_2$, $^+$NR$^3_2$, $^+$PR$^3_2$, divalent aryl, divalent fused aryl, divalent 5-membered ring heterocyclic group and divalent fused heterocyclic group;

wherein each $R^1$ is independently selected from the group consisting of: aryl, alkyl, alkaryl, araly and substituted derivatives thereof wherein the substituent in said substituted derivatives is selected from the group consisting of: carboxylic acid, alkoxy, hydroxy, alkylthio, thiol and dialkylamino;

wherein each $R^2$ and $R^3$ is independently selected from the group consisting of: aryl, alkyl, substituted aryl and substituted alkyl group;

wherein each said substituted divalent phenyl, divalent phenyl amine, biphenyl, binaphthyl and ferrocene derivative comprises at least one substituent selected from the group consisting of aryl, substituted aryl, alkyl, heteroatom, F, Cl, Br, I, $COOR^1$, $SO_3R^1$, $PO_3R^1{}_2$, $OR^1$, $SR^1$, $PR^1{}_2$, $AsR^1{}_2$, $SbR^1{}_2$, OAr, nitro, amino, vinyl, substituted vinyl and sulfonic acid;

wherein each R and R' is independently selected from the group consisting of: aryl, alkyl, alkaryl, arallkyl and substituted derivatives thereof, wherein the substituent in said substituted derivatives is selected from the group consisting of: carboxylic acid, alkoxy, hydroxy, alkylthio, thiol, dialkyl amino groups;

wherein each X and X' is independently selected from the group consisting of aryl, alkyl, alkaryl, aralkyl, alkoxy, alkoxy, hydroxy, alkylthio, thiol, primary amine, secondary amine and ArNH;

wherein each Z and Z' is independently selected from the group consisting of: halogen, alkyl, aryl, aryloxy, nitro, amino, vinyl, substituted vinyl and sulfonic acid; and wherein each Q, Q', Y, Y', T and T' is independently selected from the group consisting of aryl, alkyl, alkaryl, aralkyl and substituted derivatives thereof, wherein the sub stituent in said substituted derivatives is selected from the group consisting of: carboxylic acid, alkoxy, hydroxy, alkylthio, thiol and dialkylamino.

The present invention further includes a catalyst prepared by a process comprising contacting a transition metal salt, or a complex thereof, and a ligand selected from the group consisting of compounds represented by A through Z, AA, BB and CC, as described above.

The present invention still further includes a process for preparation of an asymmetric compound using a catalyst according to the present invention. The process comprises contacting a substrate capable of forming an asymmetric product by an asymmetric reaction and a catalyst prepared by a process comprising contacting a transition metal salt, or a complex thereof, and a ligand selected from compounds represented by A through Z, AA, BB and CC, as described above. The transition metal complexes of the chiral ligands of the present invention produce chiral products with an extremely high enantioselectivity. For example, ruthenium complex of chiral C4-TunaPhos ligand reduces isopropyl acetoacetate with 99% enantioselectivity to produce the corresponding alcohol in a 99% ee.

DETAILED DESCRIPTION OF INVENTION

This invention covers several new families of chiral biaryl phosphines. One family of chiral phosphines has a bridge to link two aryl groups such that rotation between the Sp2—Sp2 aryl—aryl bond is limited. Another family of chiral phosphines has substituents in the aryl backbone including amines and carboxylates. The steric and electronic properties of these ligands are different from those in BINAP or MeO-BIPHEP ligands. Organic, inorganic and polymer-supported biphase catalysts are also included. The chiral catalysts of the present invention are useful in a variety of transition metal-catalyzed asymmetric reactions. The various types of ligands of the present invention are described below.

For each class of A to Z, AA, BB and CC ligands, the corresponding enantiomer, as well as enantiomeric mixtures, are also contemplated. A represents chelating chiral phosphines derived from MeO-BIPHEP and related compounds, which has a bridge between two phenol unites. B and C include chiral biaryl phosphines with polymer, dendrimer and inorganic supports through the two oxygen atoms. D and E cover chiral biaryl phosphines with substituted fluorohydrocarbons or water-soluble groups. F type of ligands represent a new class of chiral biaryl phosphines with carboxylates in the 1, 1' position and G type of ligands has a bridge linked two carbonyls groups in the biaryl phosphine. Type H to K ligands have polymer supports, dendrimer supports, inorganic supports, fluorosubstitituted hydrocarbons and water-soluble groups. The linkage to the chiral biaryl ligands is a carbonyl group. Type L to O ligands have a methylene linker to polymer supports, dendrimer supports, inorganic supports, fluorine-substitituted hydrocarbons and water-soluble groups. Type N' ligands have a CF2 linker to fluorosubstitituted hydrocarbons. Type P and Q ligands include chiral biaryl phosphines with nitrogen substituents in the 1, 1' position. Type R ligands have a bridge linked to two nitrogen groups. Type S to V ligands have nitrogen linkers to connect polymer supports, dendrimer supports, inorganic supports, fluorosubstitituted hydrocarbons and water-soluble groups. Type W to Z ligands contain sulfur groups in the 1,1' position of the chiral biaryl phosphines. Type AA to BB include phosphine groups in the 1,1' position of the chiral biaryl phosphines. Type CC ligands have ortho-directed metallation groups (OMG).

The ligand of the present invention can be used in the monomeric form or in a polymeric or copolymeric form, either as a free ligand or as a ligand supported on a support material. Preferably, the support material is either a polymer support, such as, polystyrene, polyacrylate, resin, PEG, MeO-PEG, dendritic polyester or dendritic polyenamide, or the support material is an inorganic support, such as, silica, alumina, zeolite, molecular sieve or mesoporous material. The ligand may be attached to the support material through physical interactions or it can be linked to the support material by a linker group, such as, $NH(CH_2)_nSi(OEt)_3$ wherein n=1 to 8, $CO(CH_2)_nSi(OEt)_3$, $(CH_2)_nSi(OEt)_3$, C—O, C—N and $NCF_2$ linker. The ligand may be substituted by at least one water-soluble functional group, such as, sulfuric, phosphoric, carboxylic, quaternary ammonium and MeO-PEG groups.

The preferred ligands of the present invention are selected from ligands designated A through Z, AA, BB and CC, which include members represented by the formula L1 through L102, as depicted below:

L1
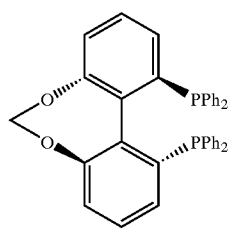
L2
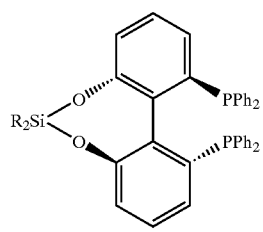
L3
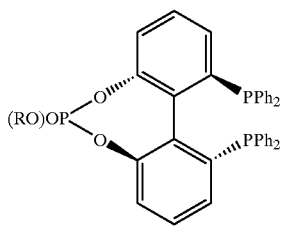
L4
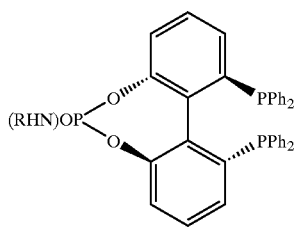
L5
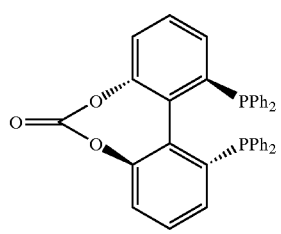
L6
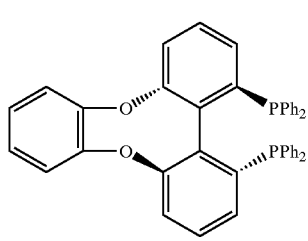
-continued
L7
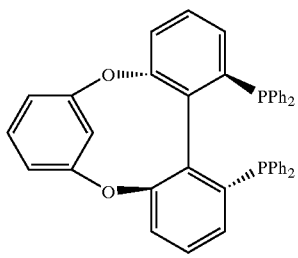
L8
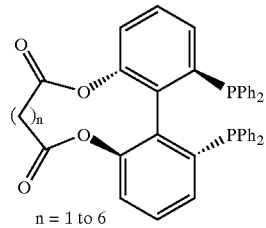
n = 1 to 6
L9
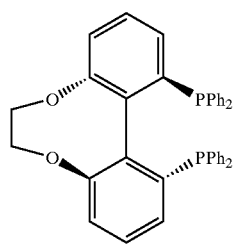
L10
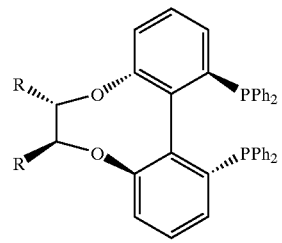
L11
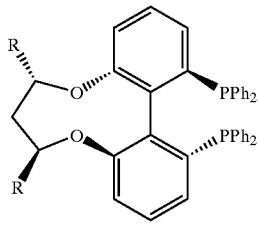
L12
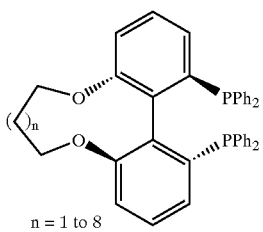
n = 1 to 8

-continued
L13
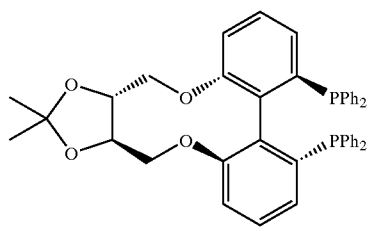
L14
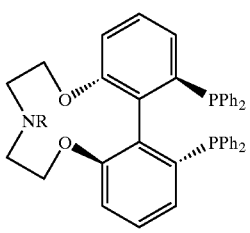
L15
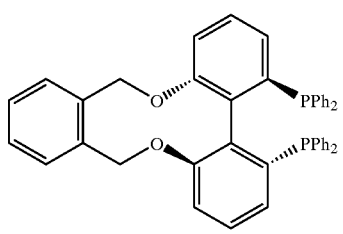
L16
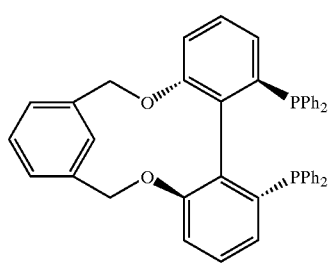
L17
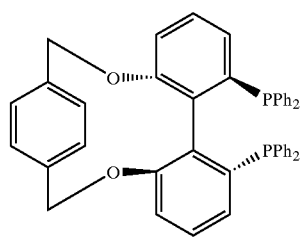
L18
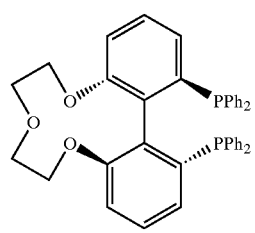
-continued
L19
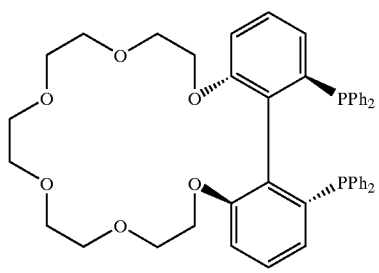
L20
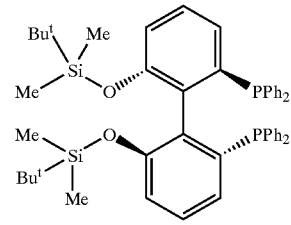
L21
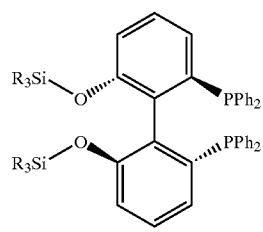
L22
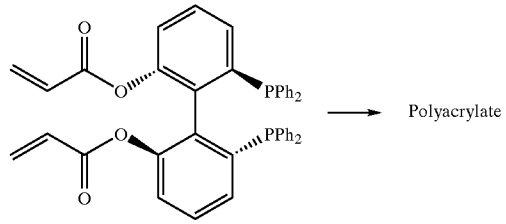 → Polyacrylate
L23
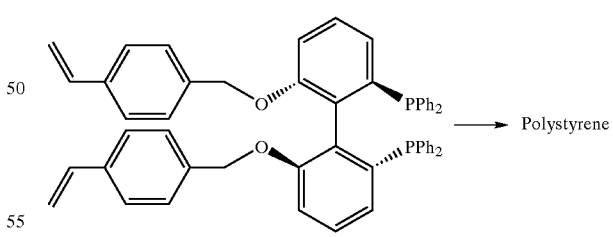 → Polystyrene
L24
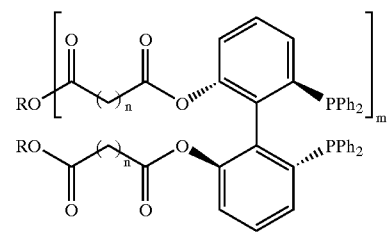

-continued

L25, L26, L27, L28, L29, L30, L31, L32, L33, L34, L35, L36

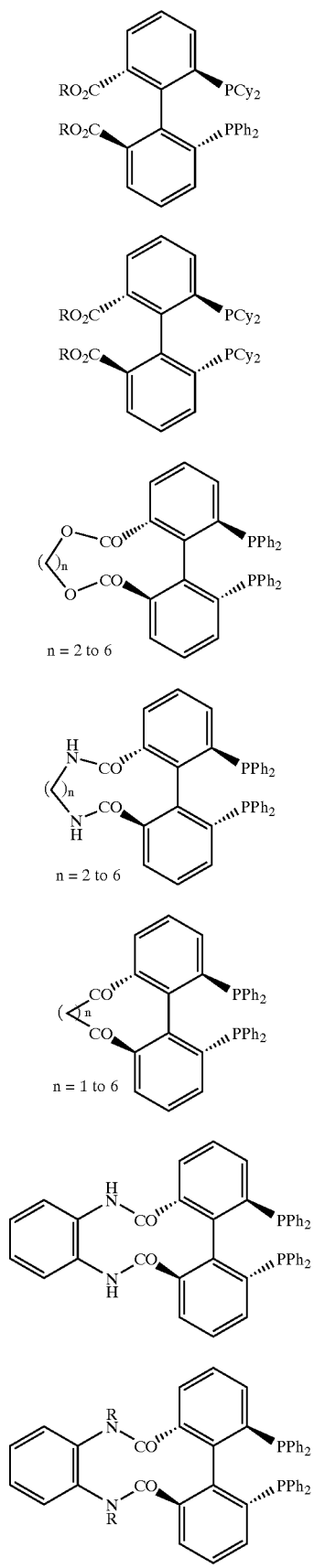
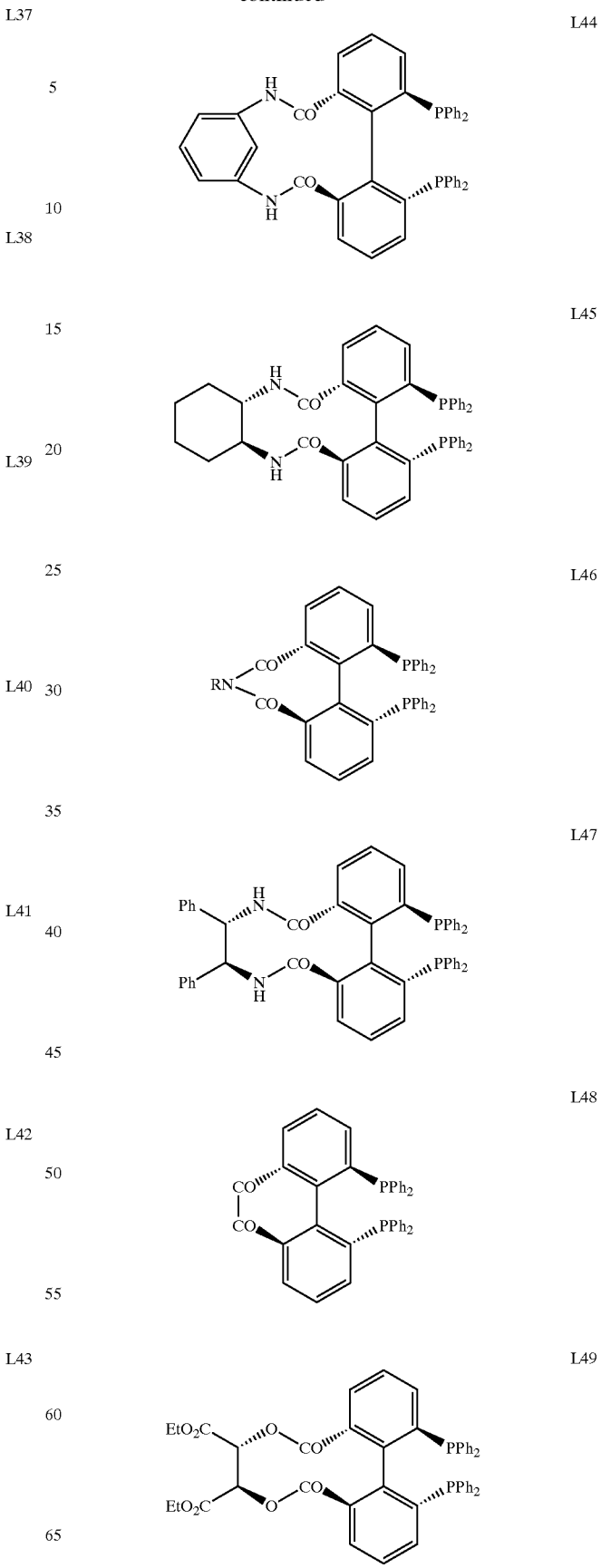

L50
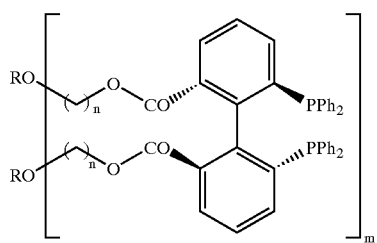
L51
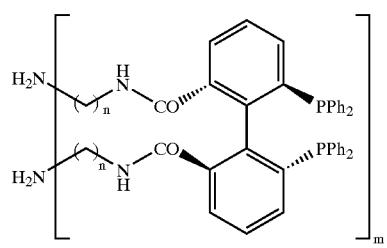
L52
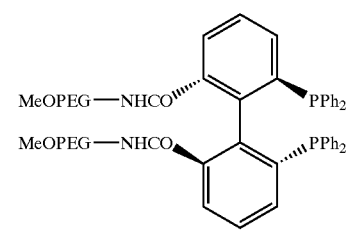
L53
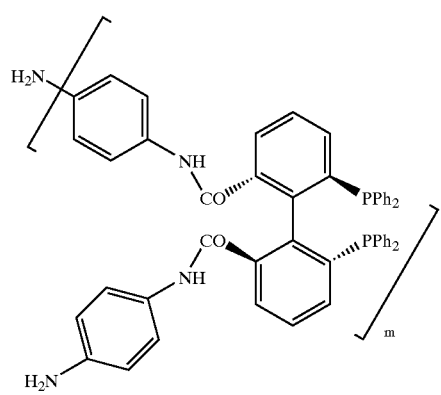
L54
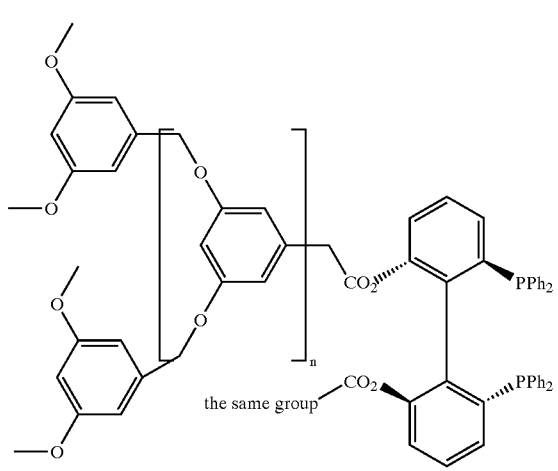
L55
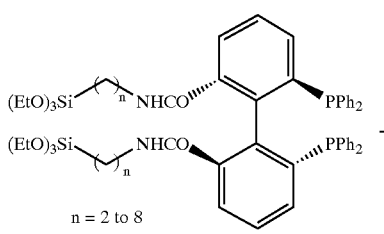
n = 2 to 8
→ SiO2 Support
Zeolite Support
Mesoporous Materials
L56
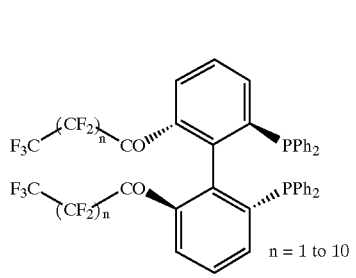
n = 1 to 10
L57
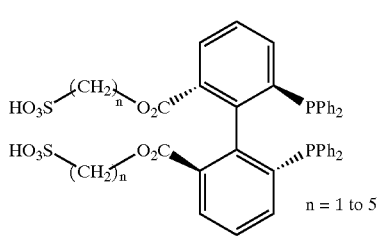
n = 1 to 5
L58
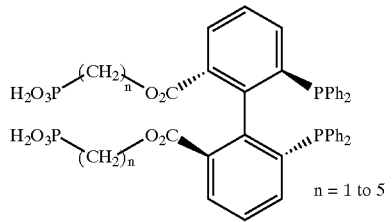
n = 1 to 5
L59
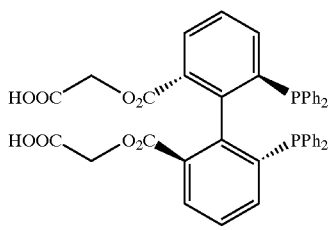
L60
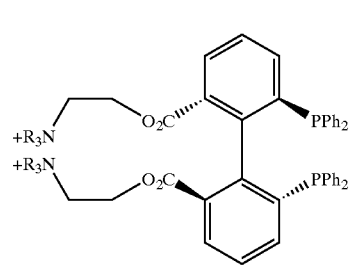

-continued
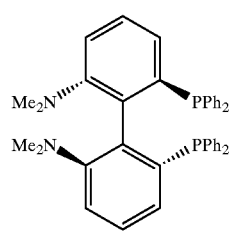
L61
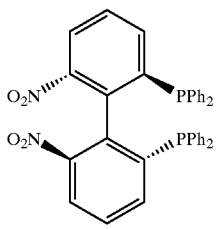
L62
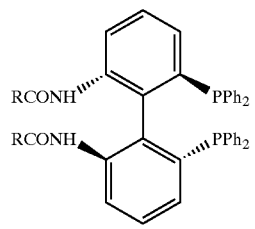
L63
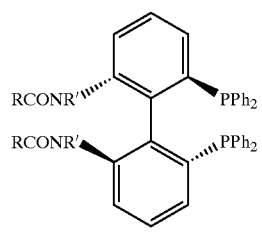
L64
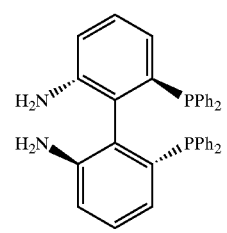
L65
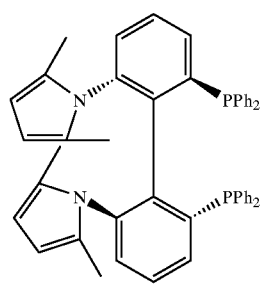
L66
-continued
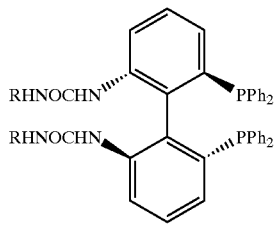
L67
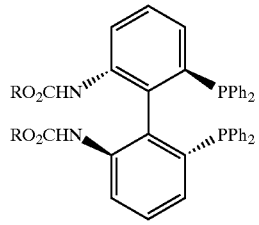
L68
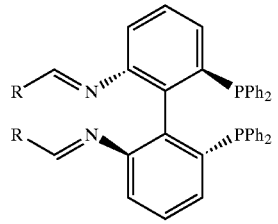
L69
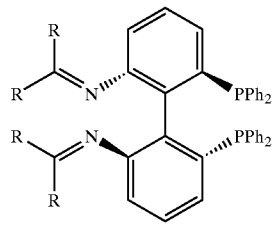
L70
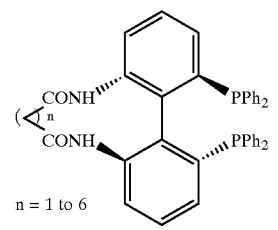
L71
n = 1 to 6
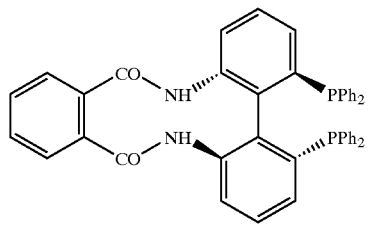
L72
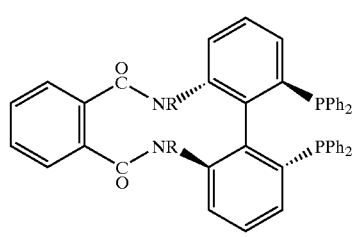
L73

L74 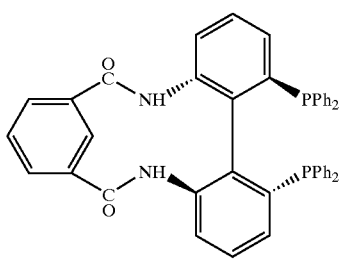
L75 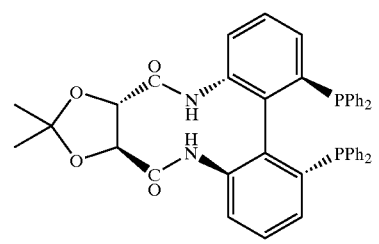
L76 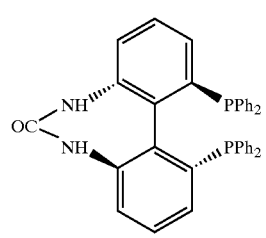
L77 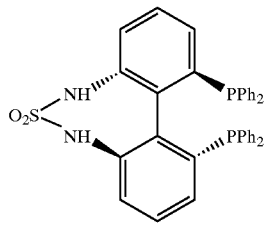
L78 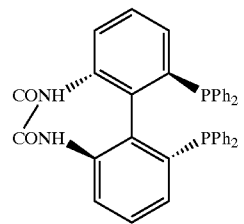
L79 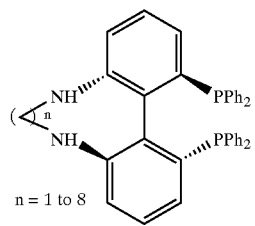
n = 1 to 8
L80 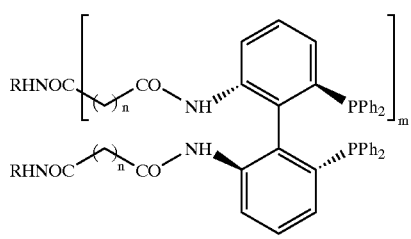
L81 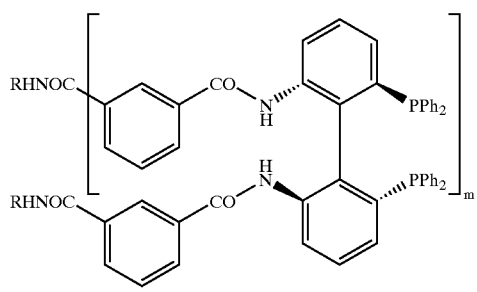
L82 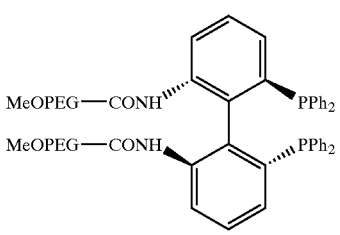
L83 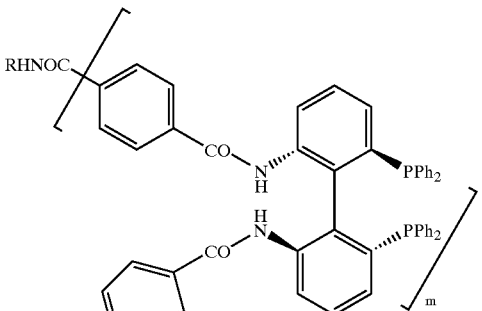
L84 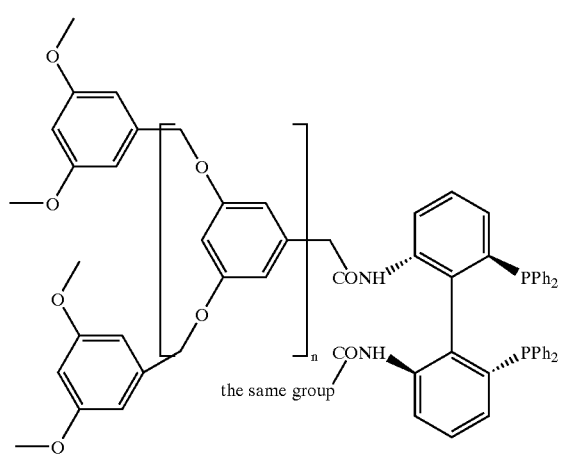
the same group L85
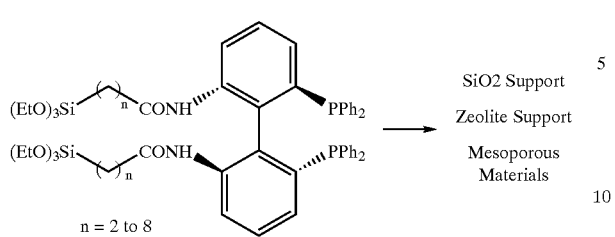
n = 2 to 8
→ SiO2 Support
Zeolite Support
Mesoporous Materials
L86
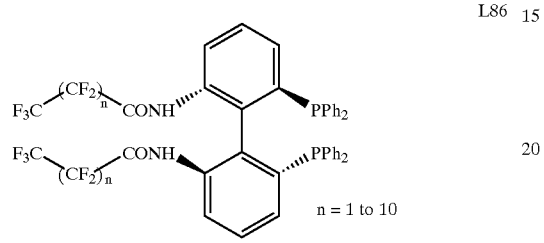
n = 1 to 10
L87
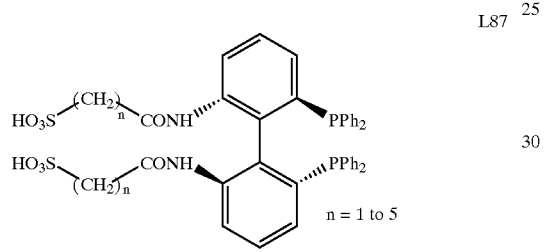
n = 1 to 5
L88
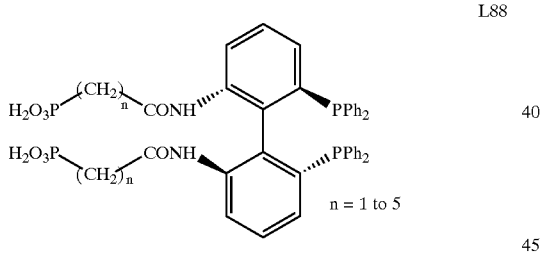
n = 1 to 5
L89
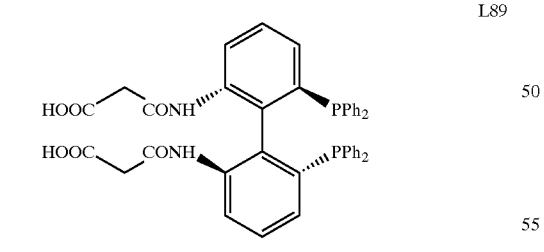
L90
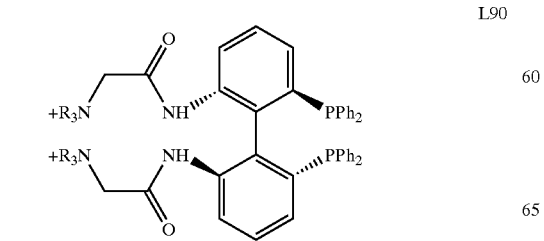
L91
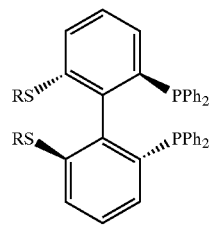
L92
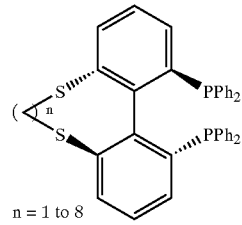
n = 1 to 8
L93
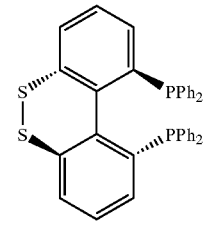
L94
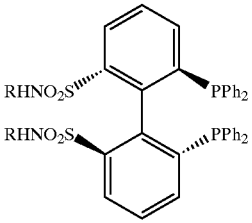
L95
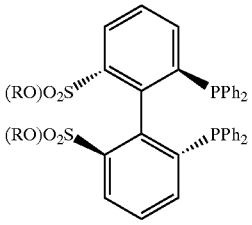
L96
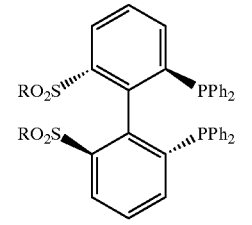
L97
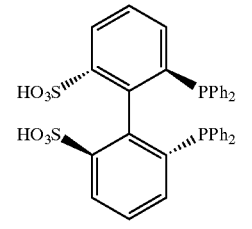

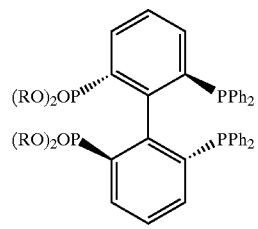
L98

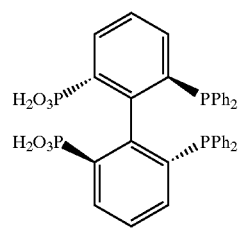
L99

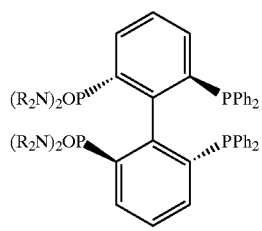
L100

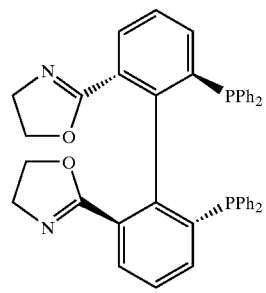
L101

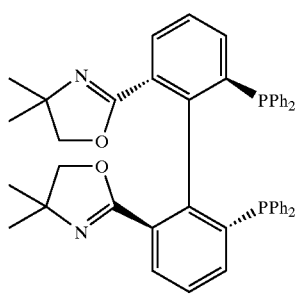
L102

The ligand may be linked to an inorganic support by any conventional links, such as, $NH(CH_2)_nSi(OEt)_3$, $CO(CH_2)_nSi(OEt)_3$, $(CH_2)_nSi(OEt)_3$ (n=1 to 8). Selective hydrolysis leads to inorganic supported ligands and catalysts. The ligand can have water-soluble functional groups, such as, $R"SO_3^-$, $R"PO_3^{2-}$, $R"COO^-$, a quaternary ammonium group and MeO-PEG, wherein R" is a ligand residue. The counterions include alkali alkaline earth metals, ammonium, halogens and triflate (Otf).

Generally, no single chiral ligand is suitable for use in all asymmetric reactions. Even with the most widely used chiral biaryl diphosphine BINAP, fine-tuning is necessary to obtain high enantiomeric excess (ee) in specific reactions. Ligands with similar stereo and electronic factors, but with different bite angles, behave dramatically differently in some reactions. For example, Kamer, P. C. J.; Reek, J. N. H. and van Leeuwen, P. W. N. M. *Chemtech*, 1998, 28(9), 27 report that in Leeuwen's nickel catalyzed hydrocyanation of styrene, the reactivity and selectivity are good only if the bite angle is in the range from 101° to 109°. Therefore, design and synthesis of new ligands has always been necessary to provide high ee in selected reactions.

Although chiral biaryl diphosphines such as BINAP, BIPHEMP, and MeO-BIPHEP are efficient ligands for some reactions, there is little or no tunability of their natural bite angle. Applications for asymmetric reactions for a wide variety of reactions and substrate are limited. Such a drawback has now been overcome by bridging the diaryl backbone with a variable length chain. For example, MeO-PHEP is an excellent starting material to construct such a bridge. After demethylation of enantiomerically pure MeO-PHEP, the dihydoxy diphosphine can react with alkyl dihalides in the presence of excess of anhydrous $K_2CO_3$ in DMF and give the desired products 1 to 6.

Synthetic routes to some chiral ligands according to the present invention are outlined below.

Method A

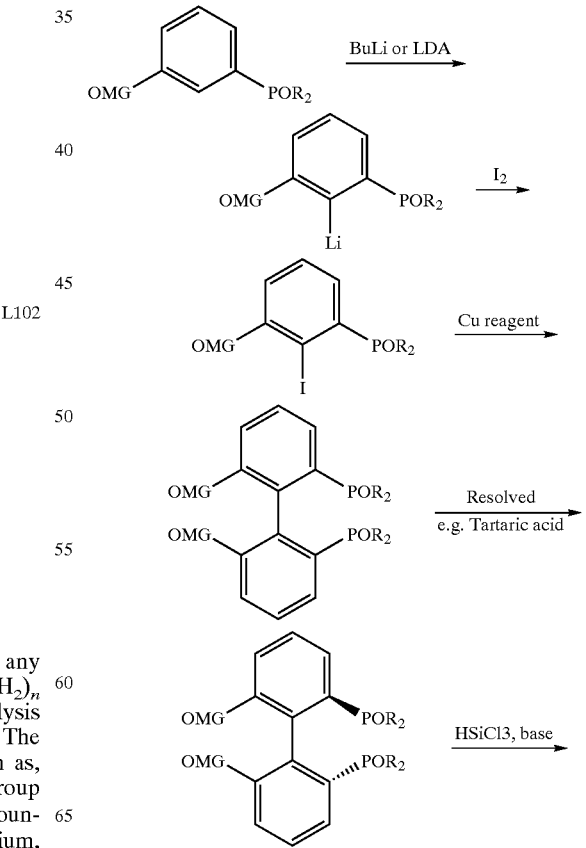

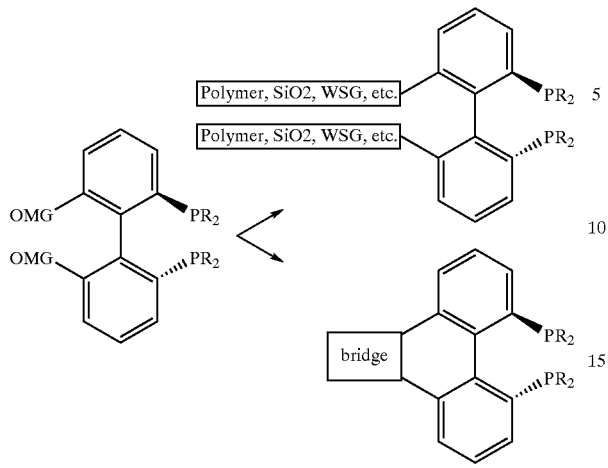
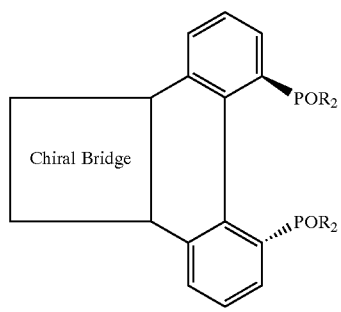

OMG=Ortho Metallation Group, e.g., R'O, RN, R'CONH COONHR', R'S, R'SO Oxazoline.
R=Ph, Cy, 3,5-dimethyl phenyl, 4-methyl phenyl.
Polymer=polystyrene, polyacrylate,
WSG=water soluble groups such as carboxylate, sulfuric acid, quaternary ammonium salts,
"Bridge" is Bridge 1, 2 or 3

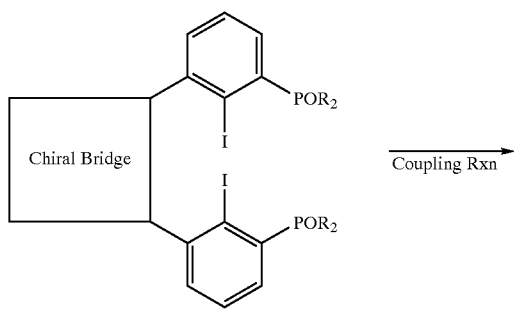

Although chiral biaryl diphosphines such as BINAP, BIPHEMP, and MeO-BIPHEP are efficient ligands for some reactions, there is little or no tunability of their natural bite angle. Applications for asymmetric reactions for a wide variety of reactions and substrate are limited. Such a drawback has now been overcome by bridging the diaryl backbone with a variable length chain.

For example, MeO-PHEP is an excellent starting material to construct such a bridge. After demethylation of enantiomerically pure MeO-PHEP, the dihydoxy diphosphine can react with alkyl dihalides in the presence of excess of anhydrous $K_2CO_3$ in DMF and give the desired products 1 to 6.

This family of phosphine ligands, here after "TunaPhos," includes members having a Cn variable length chain bridge, wherein Cn represents the number of carbon atoms in the variable length chain bridge and n is an integer. Examples of TunaPhos include TunaPhos 1 through 6, wherein the variable length chain has 1–6 carbon atoms. The calculated dihedral angles of the Cn-TunaPhos are calculated based on CAChe, MM2 program. The results of the calculations are summarized in Scheme 1 below.

Scheme 1

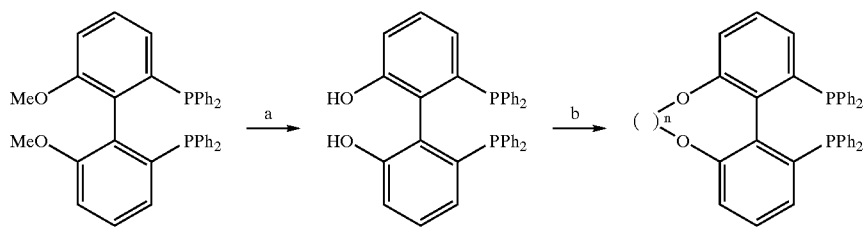

C1-TunaPhos 1
C2-TunaPhos 2
C3-TunaPhos 3
C4-TunaPhos 4
C5-TunaPhos 5
C6-TunaPhos 6 a, $BBr_3$, $CH_2Cl_2$, -78° C.~rt; b, $X(CH_2)_nX$, $K_2CO_3$, DMF

|  | c1 | c2 | c3 | c4 | c5 | c6 | TunaPhos |
| --- | --- | --- | --- | --- | --- | --- | --- |
| Natural Dihedral Angle | 60 | 74 | 77 | 88 | 94 | 106 |  |

The effect of bite angle for a reaction, asymmetric hydrogenation of β-ketoesters was carried out. The catalyst was made in situ by mixing $(Ru(benzene)Cl_2)_2$ and diphosphine ligand in hot DMF (see Kitamura, M.; Tokunaga, M.; Ohkuma, T. and Noyori R. *Tetrahedron Lett.* 1991, 32, 4163). The reactivity did not show any difference with C1 to C6 TunaPhos, but the enantioselectivity did change.

For example, when methyl acetoacetate 7 was used as the substrate and C1 or C2-TunaPhos was used as the ligand, the enantioselectivity was only about 91%. With C3-TunaPhos, the ee increased to almost 98%. The best ee (>99%) was obtained with C4-TunaPhos. With C5 and C6-TunaPhos, ee values decreased (Entry 1, Table 1). Clearly, C4-TunaPhos is a preferred ligand for hydrogenation of these types of substrates.

TABLE 1

$$R^1\text{COCH}(R^2)\text{COOR}^3 + H_2 \xrightarrow[\text{Chiral Phosphine}]{[\text{Ru}(C_6H_6)Cl_2]_2} R^1\text{CH(OH)CH}(R^2)\text{COOR}^3 \quad (\% \text{ ee})$$

7  $R^1$ = Me, $R^2$ = H, $R^3$ = Me
8  $R^1$ = Me, $R^2$ = H, $R^3$ = Pri
9  $R^1$ = Me, $R^2$ = H, $R^3$ = But
10 $R^1$ = Et, $R^2$ = Me, $R^3$ = Et
11 $R^1$ = Ph, $R^2$ = H, $R^3$ = Et
12 $R^1$ = Me, $R^2$ = Me, $R^3$ = Et
13 $R^1, R^2$ = $(CH_2)_3$, $R^3$ = Et

| Sub. | 1 | 2 | 3 | 4 | 5 | 6 | BINAP | MEOPHEP |
|---|---|---|---|---|---|---|---|---|
| 7 | 90.9 | 90.8 | 97.7 | 99.1 | 97.1 | 96.5 | 98.4 | 97.9%ee |
| 8 | 90.1 | 90.8 | 97.7 | 99.3 | 96.8 | 96.3 | 98.2 | 98.8 |
| 9 | 90.0 | 93.9 | 99.0 | 99.2 | 96.8 | 95.9 | 97.6 | 98.5 |
| 10 | 89.9 | 93.8 | 99.0 | 99.0 | 96.9 | 95.9 | 97.5 | 98.5 |
| 11 | 76.8 | 71.4 | 72.0 | 82.3 | 78.5 | 60.5 | 78.4 | 74.8 |
| 12 | 87.9 | 89.7 | 95.2 | 96.8 | 94.7 | 91.9 | 93.4 | 97.5 |
| 13 | 79.6 | 85.6 | 95.5 | 95.8 | 92.5 | 90.7 | 91.3 | 95.2 |
|  | (46.1 cis) | (45.7) | (45.5) | (45.6) | (44.2) | (46.5) | (46.8) | (45.9) |
|  | 93.9 | 95.6 | 98.5 | 98.7 | 98.0 | 97.5 | 95.7 | 98.1 |
|  | (53.9trans) | (54.3) | (54.5) | (54.4) | (55.8) | (53.5) | (53.2) | (54.1) |

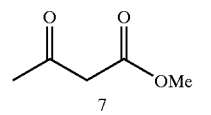
7

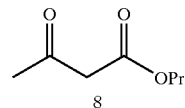
8

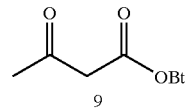
9

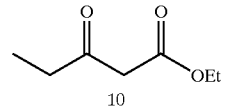
10

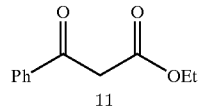
11

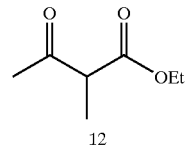
12

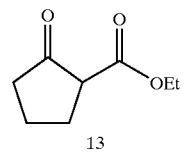
13

Based on the above results, the pronounced effect of the bite angle on the enantioselectivity in asymmetric hydrogenation of β-ketoesters is confirmed. With other types of substrates or reactions, a different bite angle and therefore, a different TunaPhos might be preferred.

The ligand according to the present invention can be racemic, i.e., racemic mixture of enantiomers, or a non-racemic mixture of enantiomers. Preferably, the ligand according to the present invention is one of the enantiomers. When the ligand is a non-racemic mixture of enantiomers, preferably it has an optical purity of at least 85% ee, more preferably, it has an optical purity of at least 95% ee.

The present invention also includes a catalyst prepared by a process comprising contacting a transition metal salt, or a complex thereof, and a ligand selected from the group consisting of compounds represented by A through Z, AA, BB and CC.

As for the ligand, the catalyst according to the present invention can be racemic, such as, a racemic mixture of enantiomers, or it can be a non-racemic mixture of enantiomers. Preferably, the catalyst according to the present invention is one of the enantiomers. When the ligand according to the present invention is a non-racemic mixture of enantiomers, preferably it has an optical purity of at least 85% ee, more preferably, it has an optical purity of at least 95% ee.

Suitable transition metals for the preparation of the catalyst include Pt, Pd, Rh, Ru, Ir, Cu, Ni, Mo, Ti, V, Re and Mn.

The catalyst can be prepared by contacting a transition metal salt or its complex and a ligand selected from A through Z, AA, BB and CC. The transition metal salt or complex can be $PtCl_2$; $Pd_2(DBA)_3$; $Pd(OAc)_2$; $PdCl_2(RCN)_2$; $(Pd(allyl)Cl)_2$; $(Rh(COD)Cl)_2$; $(Rh(COD)_2)X$; $Rh(acac)(CO)_2$; $Rh(ethylene)_2(acac)$; $Rh(CO)_2Cl_2$; $Ru(RCOO)_2(diphosphine)$; $Ru(methylallyl)2(diphosphine)$; $Ru(aryl\ group)X_2(diphosphine)$; $RuCl_2(COD)$; $(Rh(COD)_2)X$; $RuX_2(diphosphine)$; $RuCl_2(=CHR)(PR'_3)_2$; $Ru(ArH)Cl_2$; $Ru(COD)(methylallyl)_2$; $(Ir(COD)_2Cl)_2$; $(Ir(COD)_2)X$; $Cu(OTf)$; $Cu(OTf)_2$; $Cu(Ar)X$ $CuX$; $NiX_2$; $Ni(COD)_2$; $MoO_2(acac)_2$; $Ti(OiPr)_4$; $VO(acac)_2$; $MeReO_3$; $MnX_2$ or $Mn(acac)_2$; wherein each R and R' can independently be alkyl or aryl; Ar is an aryl group; and X is a counteranion. The preferred counteranions include halogen, $BF_4$, $B(Ar)_4$ wherein Ar is 3,5-di-trifluoromethyl-1-phenyl, $ClO_4$, $SbF_6$, $CF_3SO_3$, RCOO and a mixture thereof.

The catalyst may be prepared in situ or as an isolated compound. An example of the preferred catalyst of the present invention is chiral ruthenium C4-TunaPhos catalyst.

In another aspect, the present invention includes a process for preparation of an asymmetric compound using the catalysts described above. The process includes the step of contacting a substrate capable of forming an asymmetric product by an asymmetric reaction and a catalyst prepared by contacting a transition metal salt, or a complex thereof and a ligand selected from ligands represented by A through Z, AA, BB and CC.

Suitable asymmetric reactions include hydrogenation, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation.

Preferably, the asymmetric reaction is hydrogenation and the substrate to be hydrogenated is an ethylenically unsaturated compound, imine, ketone, enamine, enamide, and vinyl ester. Suitable catalysts for the hydrogenation of ketones to produce a chiral alcohol include chiral ruthenium C1 through C6 TunaPhos, particularly C4-TunaPhos catalyst.

EXAMPLES

General Procedures

All reactions and manipulations were performed in a nitrogen-filled glove box or using standard Schlenk techniques. THF and toluene were dried and distilled from sodium-benzophenone ketyl under nitrogen. Methylene chloride was distilled from $CaH_2$. Methanol was distilled from Mg under nitrogen. (R, R)-BDNPB was made a solution of 10 mg/ml in toluene before use. Column chromatography was performed using EM silica gel 60 (230–400 mesh). $^1H$, $^{13}C$ and $^{31}P$ NMR were recorded on Bruker WP-200, AM-300, and AMX-360 spectrometers. Chemical shifts were reported in ppm down field from tetramethylsilane with the solvent resonance as the internal standard. Optical rotation was obtained on a Perkin-Elmer 241 polarimeter. MS spectra were recorded on a KRATOS mass spectrometer MS 9/50 for LR-EI and HR-EI. GC analysis was carried on Hewlett-Packard 6890 gas chromatography using chiral capillary columns. HPLC analysis was carried on Waters™ 600 chromatography.

Example 1

Preparation of Ligands (R)-(6,6-Dimethoxybiphenyl-2,2'-diyl) bis (diphenylphosphine) ((R)-MeO-BIPHEP)

To a suspension of (R)-(6,6'-Dimethoxybiphenyl-2,2'-diyl) bis(diphenylphosphine oxide) (46.0 g, 74.9 mmol) in dry p-xylene (490 mL) were added $Bu_3N$ (157 mL, 660 mmol) and $HSiCl_3$ (57.1 g, 420 mmol) at room temperature under $N_2$ with stirring. After stirred at room temperature for 30 min., the mixture was heated to refluxing for 3 h. The mixture was then cooled to 0° C. and 30% aq. NaOH (350 mL, degassed) was added slowly to the mixture. $CH_2Cl_2$ (200 mL, degassed) was added and the mixture was heated to ca. 60° C. until two clear layers were formed. The water layer was removed and treated again with degassed 30% aq. NaOH (200 mL), then washed with degassed $H_2O$ (300 mL×2), brine (200 mL), dried over $Na_2SO_4$, filtered and evaporated. The residue was treated with degassed EtOH at 80° C. for 5 min, then cooled to 0° C. and filtered. The residue was washed with degassed EtOH and dried in vacuo to give the desired product (42.3 g, 97%).

$(\alpha)_D^{23}$=+42.5, (c=1.0, $CHCl_3$) $^1NMR(CDCl_3)$: δ 7.21–7.12 (m, 18H), 7.03–6.95 (m, 4H), 6.70–6.65 (m, 4H), 3.08 (s, 6H); $^{31}P$ NMR ($CDCl_3$): δ −14.2; $^{13}C$ NMR ($CDCl_3$): δ 157.5–127.8 (m, Ar-C), 110.7, 54.7.

(R)-(6,6'-Dihydroxybiphenyl-2,2'-diyl) bis (diphenylphoshine) ((R)-HO-BIPHEP)

A solution of (S)-(6,6'-dimethoxybiphenyl-2,2'-diyl)bis (diphenylphosphine) ((R)-MeO-BIPHEP) (23.3 g, 40 mmol) in $CH_2Cl_2$ (500 mL) was cooled to −78° C. and purged with $N_2$ for 15 min, $BBr_3$ (30.0 g, 120 mmol) was added via a syringe over a period of 10 min. The solution was stirred at −78° C. for 1 h, and was warmed slowly to room temperature overnight. Then the mixture was cooled to 0° C. and degassed water (120 mL) was added slowly until two clear layers were formed. The aqueous layer was removed and the organic layer was washed subsequently with degassed $H_2O$ (200 mL×2), brine (200 mL) and dried over $Na_2SO_4$. The organic layer was passed through a pad of neutral $Al_2O_3$ and evaporated to dryness, the solid thus obtained was essentially pure and directly used for the next step.

$(\alpha)_D^{23}$=−10.4, (c=0.5, EtOH) $^1$H NMR (CD$_2$Cl$_2$): δ 7.3–6.8 (m, 26H), 4.27 (s, br, 2H); $^{31}$P NMR (CD$_2$Cl$_2$): δ −13.6; $^{13}$C NMR(CD$_2$Cl$_2$): δ 154.9–116.7 (i, Ar-C). HRMS: 555.1649, Calcd. for (M$^+$1): 555.1643.

General Procedure for (R)-(6,6'-Alkylene-2,2'-diyl) bis(diphenylphosphine) ((R)-(CH$_2$)$_n$-TunaPhos)

A solution of (R)-(6,6'-Dihydroxybiphenyl-2,2'-diyl) bis (diphenylphosphine) ((R)-HO-BIPHEP) (1.11 g, 2 mmol) in DMF (20 mL) was purged with N$_2$ for 15 Min., anhydrous K$_2$CO$_3$ (1.38 g, 10 mmol) was added as a solid and stirred at room temperature for 15 min. Bromochloromethane (2.1 mmol) was added via a syringe and stirred at room temperature for 24 h, then heated to 60° C., stirred until the starting material was completely consumed (~48 h). The solvent was removed under vacuum and the residue was extracted with ether (100 mL), washed with water (20 mL×2), brine (20 mL) and dried over Na$_2$SO$_4$. After removal of the solvent, the foamy solid was purified by flash chromatography on a silica gel with CH$_2$Cl$_2$-hexanes (1:3) as eluent. C3, C4, C5, C6-TunaPhos could be made using this procedure. For the synthesis of C2 TunaPhos, up to 3.5 eq. of 1,2-dibromoethane was used to make a complete conversion of the starting material.

C1-TunaPhos (1)

$(\alpha)_D^{23}$=−396, (c=0.5, CHCl$_3$); $^1$H NMR (CDCl$_3$): δ 7.8–7.0 (m, 26H), 5.41 (s, 2H); $^{31}$P NMR (CDCl$_3$): δ −9.7; $^{13}$C NMR(CDCl$_3$): δ 152.9–121.0 (m, Ar-C), 101.6; HRMS: 567.1672) Calcd. for (M$^+$+1): 567.1643.

C2-TunaPhos (2)

$(\alpha)_D^{23}$=−294, (c=0.5, CHCl$_3$); $^1$H NMR (CDCl$_3$): δ 7.8–7.0 (m, 26H), 4.30 (d, 2H, J=8.7 Hz), 4.00 (d, 2H J=8.7 Hz); $^{31}$P NMR (CDCl$_3$): δ −8.4; $^{13}$C N(CDCl$_3$): δ 159.8–122.4 (m, Ar-C), 74.3; HRMS: 581.1816, Calcd. for (M$^+$+1): 581.1799.

C3-TunaPhos (3)

$(\alpha)_D^{23}$=−225, (c=0.5, CHCl$_3$); $^1$H NMR (CDCl$_3$): δ 7.5–6.7 (m, 26H), 4.1–4.0 (d, 4H), 1.68(t, J=5.7 Hz , 2H); $^{31}$P NMR (CDCl$_3$): δ −8.7; $^{13}$C NR(CDCl$_3$): δ 157.8–118.8 (m, Ar-C), 72.2, 29.6; HRMS: 595.1922, Calcd. for (M$^+$+1): 595.1956.

C4-TunaPhos (4)

$(\alpha)_D^{23}$=−167, (c=0.5, CHCl$_3$); $^1$H NMR (CDCl$_3$): δ 7.6–6.7 (m, 26H), 4.19(d, J=11.5 Hz, 2H), 3.77(d, J=10.4 Hz, 2H), 1.68(t, J=10.4 Hz, 2H), 1.55(d, J=11.5 Hz, 2H); $^{31}$P NMR (CDCl$_3$): δ −11.2; $^{13}$C NMR(CDCl$_3$): δ156.3–115.5 (m, Ar-C), 69.7, 25.5; HRMS: 609.2100, Calcd. for (M$^+$+1): 609.2112.

C5-TunaPhos (5)

$(\alpha)_D^{23}$=−143, (c=0.5, CHCl$_3$); $^1$H NMR (CDCl$_3$): δ 7.6–6.9 (m, 26H), 4.3–4.2 (m, 2H), 4.0–3.8 (m, 2H), 1.9–1.4 (m,6H); $^{31}$P NMR (CDCl$_3$): δ −11.4; $^{13}$C NMR(CDCl$_3$): δ 157.0–113.5(m, Ar-C), 67.2, 26.0, 22.3; HRMS: 623.2261, Calcd. For (M$^+$+1): 623.2269.

C6-TunaPhos (6)

$(\alpha)_D^{23}$=−122, (c=0.5, CHCl$_3$); $^1$H NMR (CDCl$_3$): δ 7.8–6.8 (m, 26H), 4.1–4.0(m, 2H), 3.7–3.6 (m, 2H), 1.9–1.4 (m, 8H); $^{31}$P NMR (CDCl$_3$): δ −11.5; $^{13}$C NMR(CDCl$_3$): δ 156.5–111.4(m, Ar-C), 66.4, 25.9, 24.5; HRMS: 637.2413, Calcd. for (M$^+$+1): 637.2425.

Example 2

Asymmetric Hydrogenation

To a 10 mL Schlenk tube was added (Ru(benzene)Cl$_2$)$_2$ (10 mg, 0.02 mmol) and diphosphine (0.048 mmol of R-BINAP, R-MeOPHEP or C1–C6 TunaPhos) and then the tube was purged with N$_2$ three times. Freshly distilled and degassed DMF (1 mL) was added to this tube. The resulting mixture was heated at 99–101° C. for 10 min., then cooled to 50° C. and the solvent was removed under vacuum. An orange to dark red solid was obtained, this solid was used directly as the catalyst. The catalyst was taken into a glove box and dissolved in degassed methanol (8 mL) and distributed equally to 8 vials (5 mL each). The β-ketoester was added, the mixture was sealed in a bomb and taken out of the glove box. The bomb was purged three times with H$_2$, then the pressure was set to 750 psi. The reactor was set in an oil bath at 60° C. and was stirred for 20 h. The bomb was then cooled with an ice-bath, and H$_2$ was carefully released. The methanol solution was transferred to a 25 mL pear-shaped flask. After the removal of methanol, ether (20 mL) was added and the solution was washed with H$_2$O (3×mL), brine (3 mL), and dried over Na$_2$SO$_4$. The ether solution was passed through a short silica-gel column and concentrated to dryness before analysis.

Example 3

Asymmetric Heck Reaction

Asymmetric Heck reaction is an attractive C—C bond forming reaction. A typical Pd-catalyzed Heck reaction was carried out with BINAP, MeO-BIPHEP and TunaPhos ligands, the results are outlined in Table 2.

With the TunaPhos ligands possessing an even number of methylene groups give better ee's than TunaPhos ligands with an odd number of methylene groups. Accordingly, in the standard asymmetric Heck reaction (phenyl triflate and 2,3-dihydrofuran as substrates), using C1-TunaPhos as ligand, 69.7% ee was obtained while 90.5% ee was obtained with C6-TunaPhos.

TABLE 2

Heck Reaction: Ligand Effect[a]

| Phosphine[b] | A:B | A (ee %) | B (ee %) |
|---|---|---|---|
| Binap | 95:5 | 79.0 | 61.5 |
| MeO-Phep | 94:6 | 88.8 | 31.5 |
| C1-Tunaphos | 94:6 | 69.7 | 10.8 |
| C2-Tunaphos | 98:2 | 78.4 | 35.7 |
| C3-Tunaphos | 95:5 | 72.6 | 24.5 |
| C4-Tunaphos | 96:4 | 88.8 | 62.8 |
| C5-Tunaphos | 91:9 | 75.2 | 24.1 |
| C6-Tunaphos | 95:5 | 90.5 | 61.6 |

[a]All of the reactions were run with a ratio of PhOTf:2,3-dihydrofuran:Pr$^i_2$NEt:Pd(OAc)$_2$:Phosphine = 1:5:3:0.03:0.063, in 2 ml of benzene for 40 h;
[b]R-phosphines were used.

Under these conditions, C6-TunaPhos was used as the ligand to test various substrates. The result are summarized in Table 3.

TABLE 3

Asymmetric Heck reaction with C6-TunaPhos

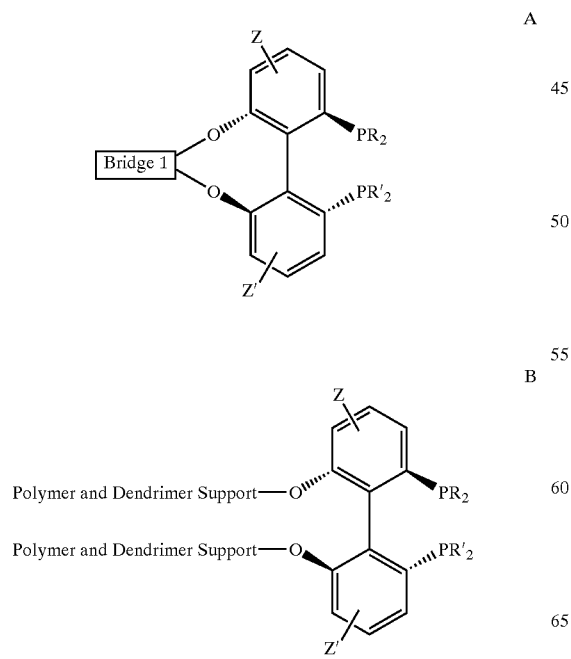

| R | yield | 1:2 | 1 (ee %) | 2 (ee %) |
|---|---|---|---|---|
| CF$_3$ | 91% | 92:8 | 96.3 | 47.5 |
| NO$_2$ | 93% | 91:9 | 95.8 | 42.0 |
| CN | 88% | 92:8 | 91.2 | 60.2 |
| Cl | 90% | 90:10 | 93.2 | 59.6 |
| CH$_3$ | a | 97:3 | 91.4 | n/a |
| Br | a | 84:16 | 93.3 | 0 |
| OTf | | 82:18 | 92.0 | 34.0 | a Low conversion (~20%)

Alternative work-up and isolation procedures are also possible, and will be evident to those skilled in the art.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A ligand selected from the group consisting of compounds represented by A through Z, AA, BB and CC:

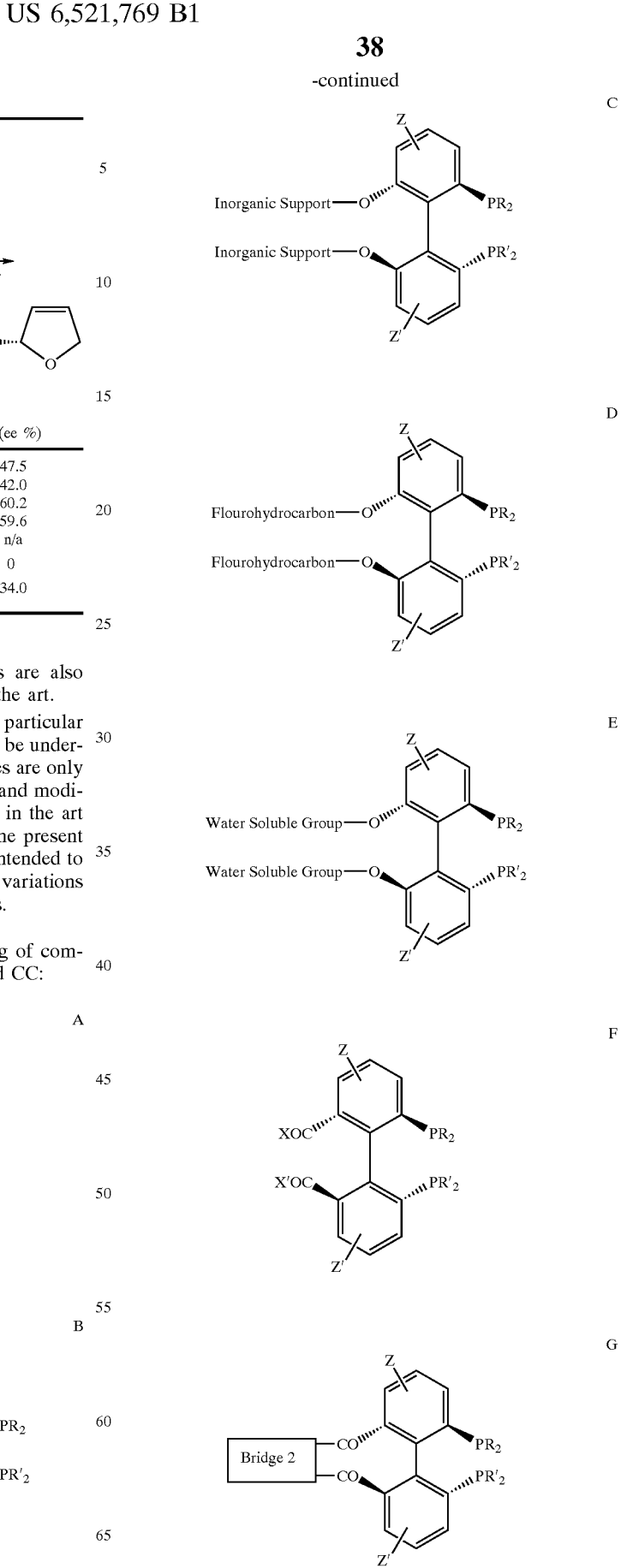

H
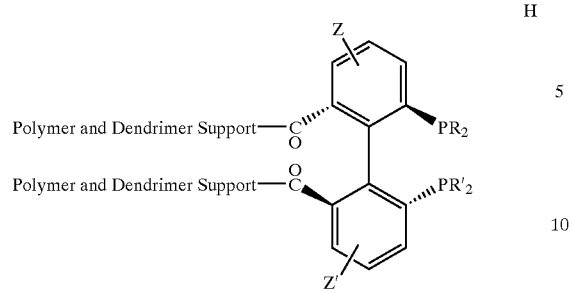
M
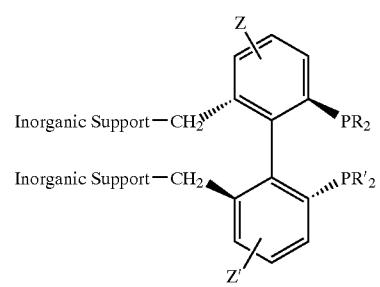
I
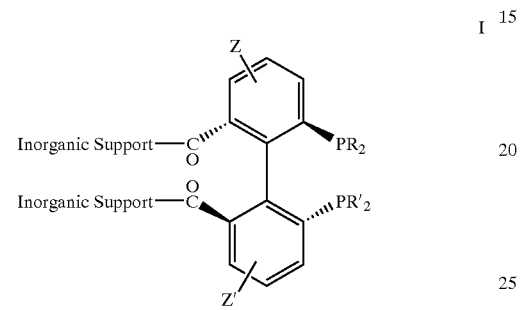
N
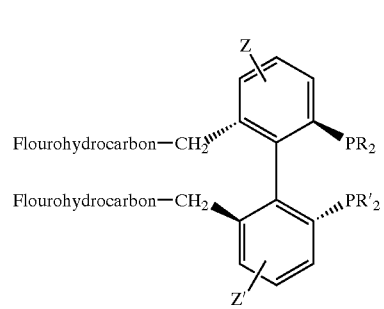
J
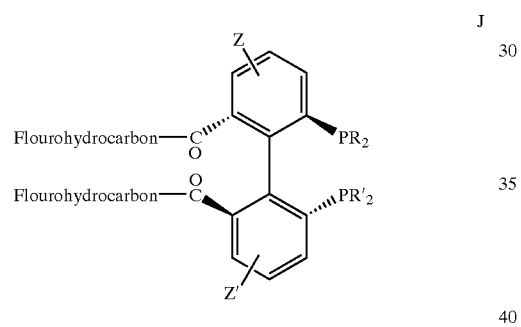
O
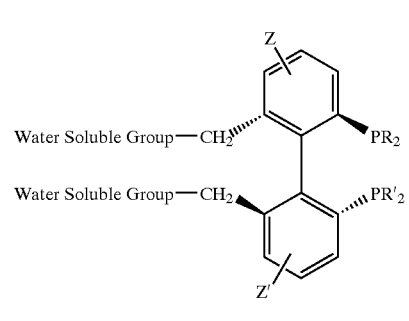
K
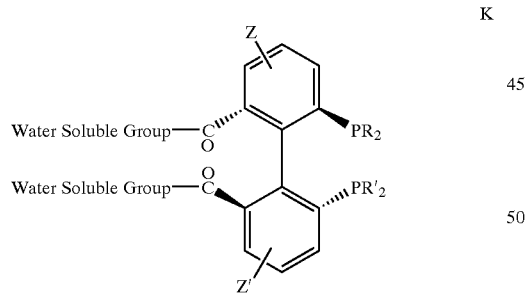
P
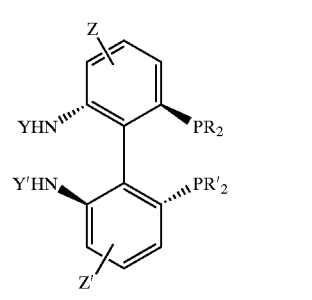
L
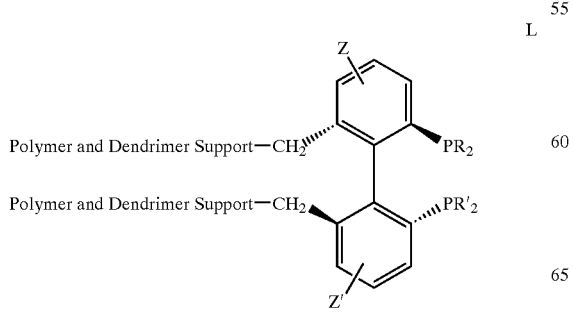
Q
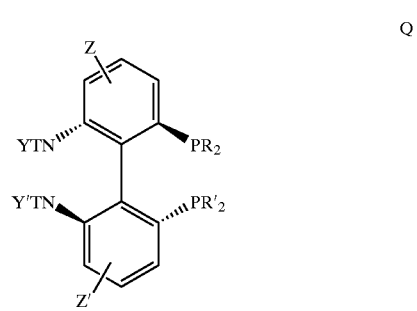

| 41 -continued | | 42 -continued | |
|---|---|---|---|
| 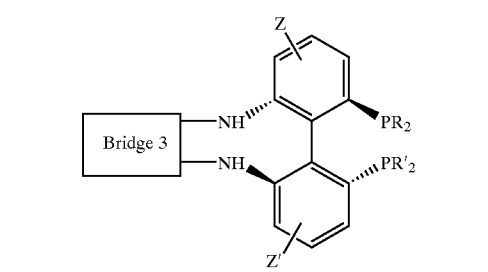 | R | 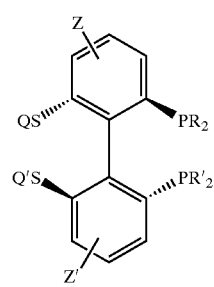 | W |
| 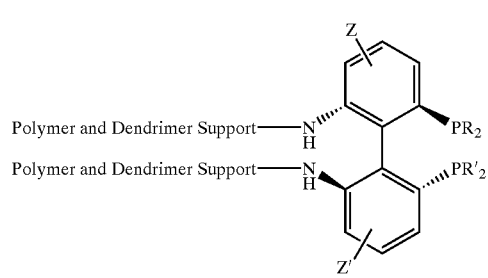 | S | 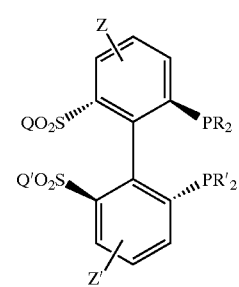 | X |
| 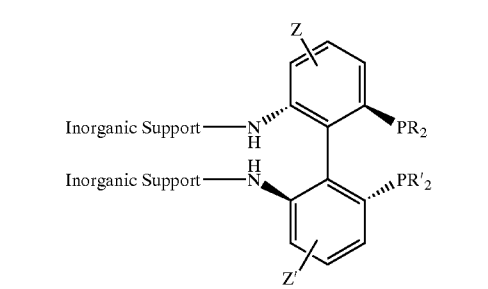 | T | 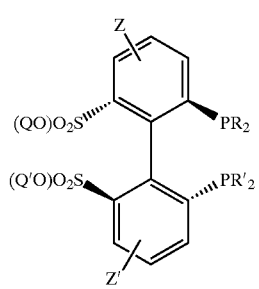 | Y |
| 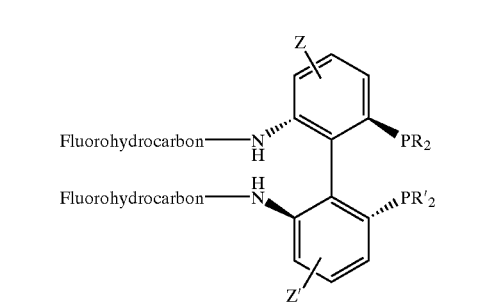 | U | 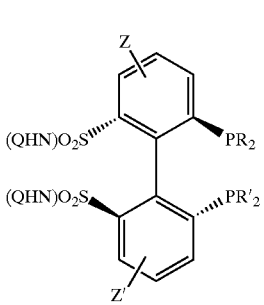 | Z |
| 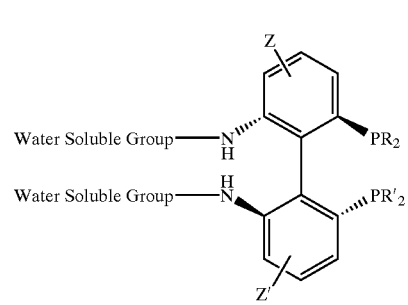 | V | 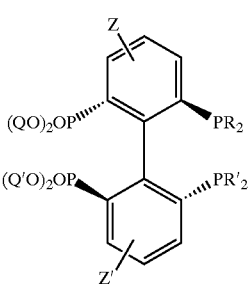 | AA |

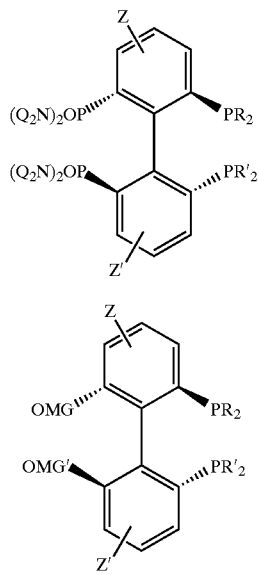

BB

CC wherein "bridge 1" is selected from the group consisting of: C=O, C=S, SO$_2$, PO(OR$^1$), PO(NHR$^1$), PO(NR$^1$R$^2$), divalent phenyl, substituted divalent phenyl, 2,2'-divalent-1,1'-biphenyl, substituted 2,2'-divalent-1,1'-biphenyl, 2,2'-divalent-1,1'-binaphthyl, substituted 2,2'-divalent-1,1'-binaphthyl, 1,1'-ferrocene, substituted 1,1'-ferrocene, SiR$^1_2$ (CH$_2$)$_n$ where n is an integer ranging from 1 to 8, and (CR$^2_2$)$_n$X$^1$(CR$^2_2$)$_m$ wherein each n, m is independently an integer from 1 to 8, wherein X$^1$ is selected from the group consisting of: O, S, NR$^3$, PR$^3_2$, $^+$NR$^3_2$, $^+$PR$^3_2$, divalent aryl, divalent fused aryl, divalent 5-membered ring heterocyclic group and divalent fused heterocyclic group;

wherein "bridge 2" is selected from the group consisting of: NH, O, a single bond, (CH$_2$)$_n$, O(CH$_2$)$_n$O, NH(CH$_2$)$_n$NH, wherein each n is independently an integer from 1 to 8, divalent phenyl, substituted divalent phenyl, divalent phenyl amine, substituted divalent phenyl amine, 2,2'-divalent-1,1'-biphenyl, substituted 2,2'-divalent-1,1'-biphenyl, 2,2'-divalent-1,1'-binaphthyl, substituted 2,2'-divalent-1,1'-binaphthyl, 1,1'-ferrocene, substituted 1,1'-ferrocene, O(CR$^2_2$)$_n$X$^1$(CR$^2_2$)$_m$O, NH(CR$^2_2$)$_n$X$^1$(CR$^2_2$)$_m$NH and (CR$^2_2$)$_n$X$^1$(CR$^2_2$)$_m$ wherein each n, m is independently an integer from 1 to 8, wherein X$^1$ is selected from the group consisting of: O, S, NR$^3$, PR$^3_2$, $^+$NR$^3_2$, $^+$PR$^3_2$, divalent aryl, divalent fused aryl, divalent 5-membered ring heterocyclic group and divalent fused heterocyclic group;

wherein "bridge 3" is selected from the group consisting of: SO$_2$, CO, COCO, OC(CH$_2$)$_n$CO, (CH$_2$)$_n$ wherein n is an integer ranging from 1 to 8, COArCO, wherein Ar is selected from the group consisting of: divalent phenyl, substituted divalent phenyl, 2,2'-divalent-1,1'-biphenyl, substituted 2,2'-divalent-1,1'-biphenyl, 2,2'-divalent-1,1'-binaphthyl, substituted 2,2'-divalent-1,1'-binaphthyl, 1,1'-ferrocene, substituted 1,1'-ferrocene and CO(CR$^2_2$)$_n$X$^1$(CR$^2_2$)$_m$CO wherein each n, m is independently an integer from 1 to 8, wherein X$^1$ is selected from the group consisting of: O, S, NR$^3$, PR$^3_2$, $^+$NR$^3_2$, $^+$PR$^3_2$, divalent aryl, divalent fused aryl, divalent 5-membered ring heterocyclic group and divalent fused heterocyclic group;

wherein each R$^1$ is independently selected from the group consisting of: aryl, alkyl, alkaryl, aralkyl and substituted derivatives thereof wherein the substituent in said substituted derivatives is selected from the group consisting of: carboxylic acid, alkoxy, hydroxy, alkylthio, thiol and dialkylamino;

wherein each R$^2$ and R$^3$ is independently selected from the group consisting of: aryl, alkyl, substituted aryl and substituted alkyl group;

wherein each said substituted divalent phenyl, divalent phenyl amine, biphenyl, binaphthyl and ferrocene derivative comprises at least one substituent selected from the group consisting of aryl, substituted aryl, alkyl, heteroatom, F, Cl, Br, I, COOR$^1$, SO$_3$R$^1$, PO$_3$R$^1_2$, OR$^1$, SR$^1$, PR$^1_2$, AsR$^1_2$, SbR$^1_2$, OAr, nitro, amino, vinyl, substituted vinyl and sulfonic acid;

wherein each R and R' is independently selected from the group consisting of: aryl, alkyl, alkaryl, aralkyl and substituted derivatives thereof, wherein the substituent in said substituted derivatives is selected from the group consisting of: carboxylic acid, alkoxy, hydroxy, alkylthio, thiol, dialkyl amino groups;

wherein each X and X' is independently selected from the group consisting of: aryl, alkyl, alkaryl, aralkyl, alkoxy, alkoxy, hydroxy, alkylthio, thiol, primary amine, secondary amine and ArNH;

wherein each Z and Z' is independently selected from the group consisting of: hydrogen, halogen, alkyl, aryl, aryloxy, nitro, amino, vinyl, substituted vinyl and sulfonic acid; and wherein each Q, Q', Y, Y', T and T' is independently selected from the group consisting of: aryl, alkyl, alkaryl, aralkyl and substituted derivatives thereof, wherein the substituent in said substituted derivatives is selected from the group consisting of: carboxylic acid, alkoxy, hydroxy, alkylthio, thiol and dialkylamino.

2. The ligand of claim 1, wherein said ligand is a racemic mixture of enantiomers.

3. The ligand of claim 1, wherein said ligand is a non-racemic mixture of enantiomers.

4. The ligand of claim 1, wherein said ligand is one of the enantiomers.

5. The ligand of claim 1, having an optical purity of at least 85% ee.

6. The ligand of claim 1, having an optical purity of at least 95% ee.

7. The ligand of claim 1, wherein said ligand is in a polymeric or copolymeric form.

8. The ligand of claim 1, wherein said ligand is supported on a support material.

9. The ligand of claim 8, wherein said support is a polymer support.

10. The ligand of claim 9, wherein said polymer support is selected from the group consisting of polystyrene, polyacrylate, resin, PEG, MeO-PEG, dendritic polyester and dendritic polyenamide.

11. The ligand of claim 8, wherein said support is an inorganic support.

12. The ligand of claim 11, wherein said inorganic support is a mesoporous material.

13. The ligand of claim 11, wherein said inorganic support is selected from the group consisting of: silica, alumina, zeolite and molecular sieve.

14. The ligand of claim 8, wherein said ligand is linked to a support material by a linker group.

15. The ligand of claim 8, wherein said linker is selected from the group consisting of: NH(CH$_2$)$_n$Si(OEt)$_3$, CO(CH$_2$)$_n$Si(OEt)$_3$, (CH$_2$)$_n$Si(OEt)$_3$, C—O, C—N and and NCF$_2$ linker, wherein n=1 to 8.

16. The ligand of claim 1, including at least one water soluble functional group.

17. The ligand of claim 1, wherein said water-soluble functional group is selected from the group consisting of sulfuric, phosphoric, carboxylic, quaternary ammonium and MeO-PEG.

18. A ligand selected from the group consisting of:

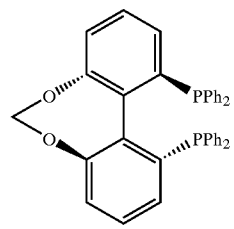
L1

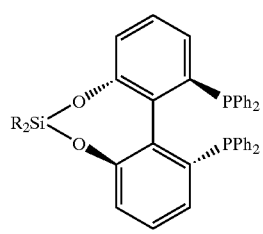
L2

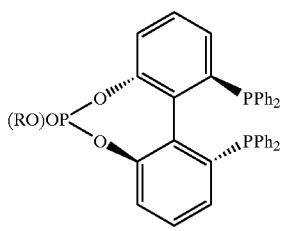
L3

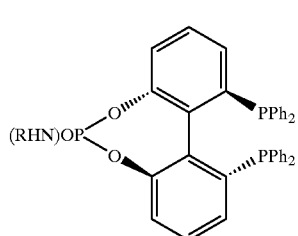
L4

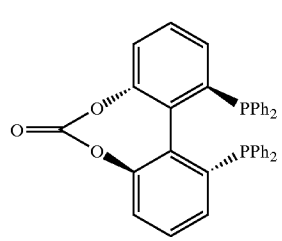
L5

-continued

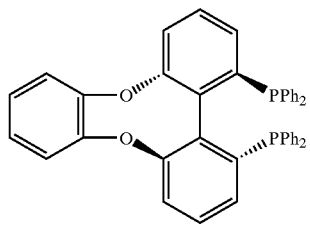
L6

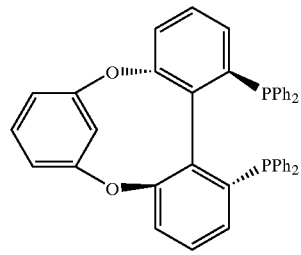
L7

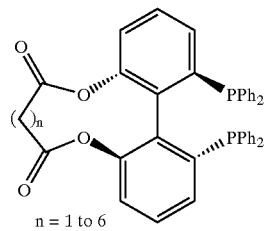
L8 n = 1 to 6

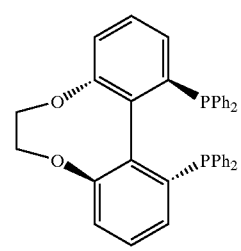
L9

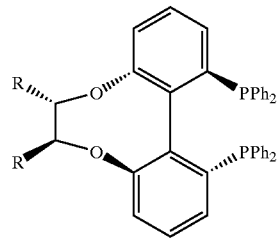
L10

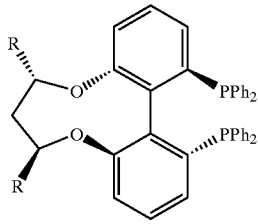
L11

L12
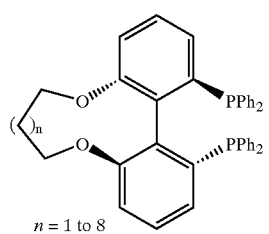
n = 1 to 8
L13
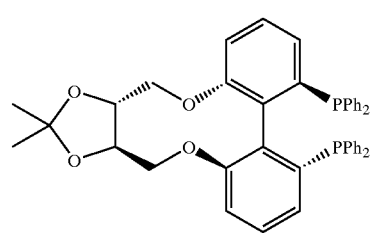
L14
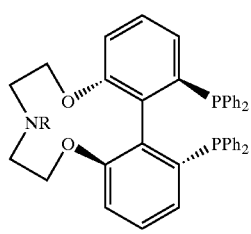
L15
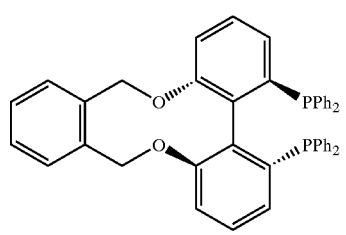
L16
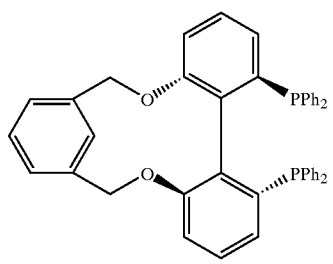
L17
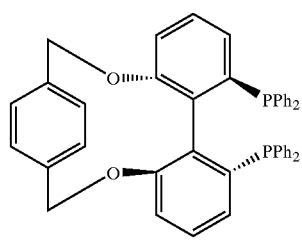
L18
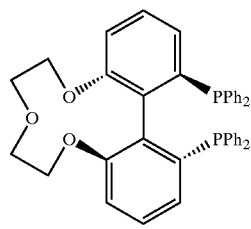
L19
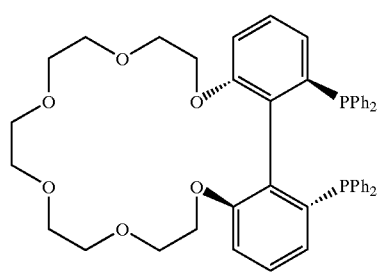
L20
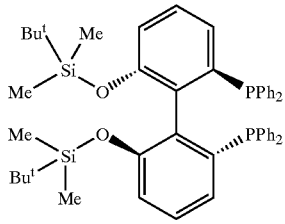
L21
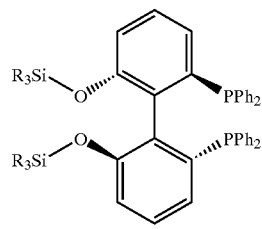
L22
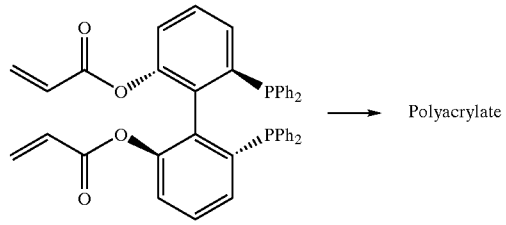 → Polyacrylate
L23
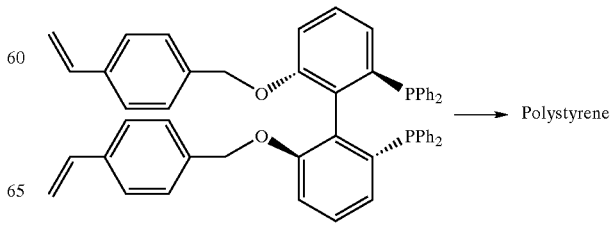 → Polystyrene

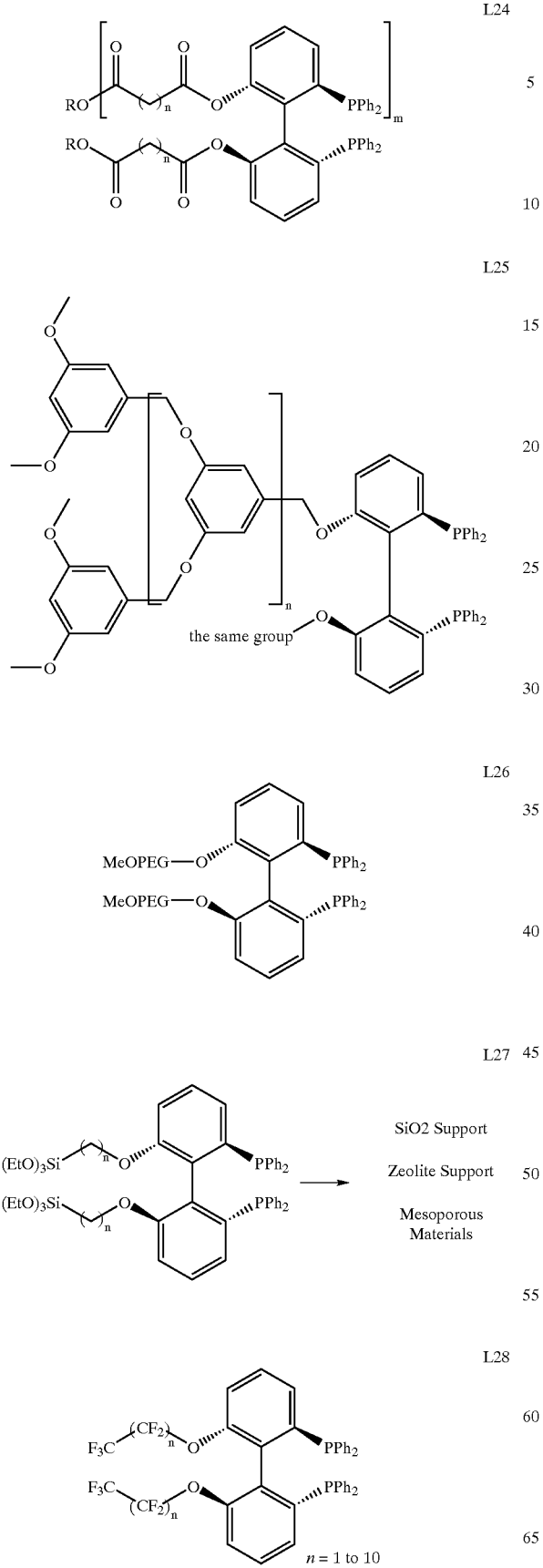
L24
L25
L26
L27
L28
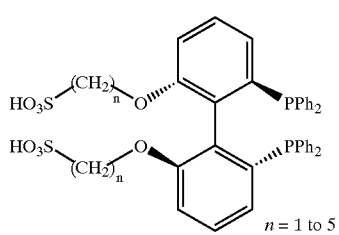
L29
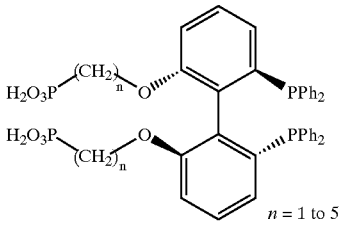
L30
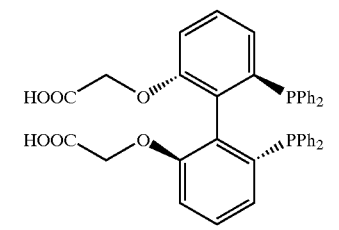
L31
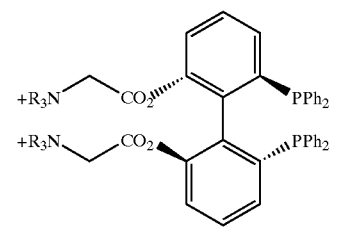
L32
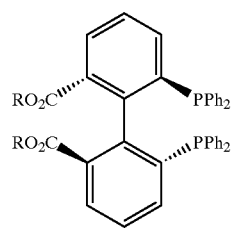
L33
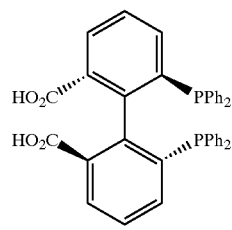
L34
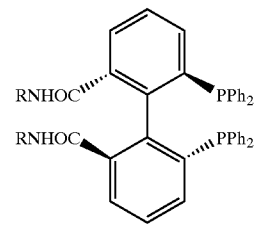
L35

-continued
L36
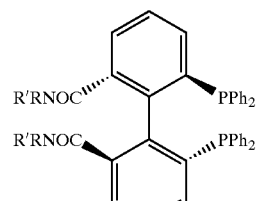
L37
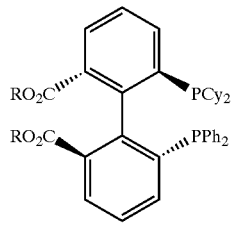
L38
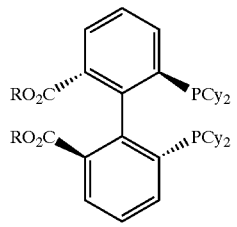
L39
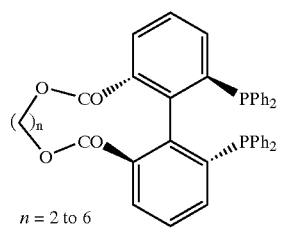
n = 2 to 6
L40
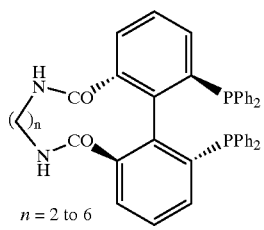
n = 2 to 6
L41
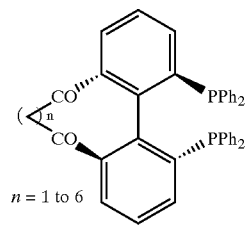
n = 1 to 6
L42
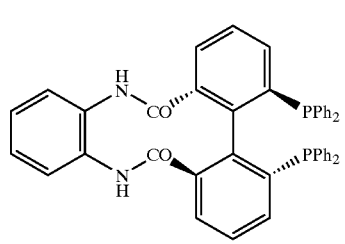
-continued
L43
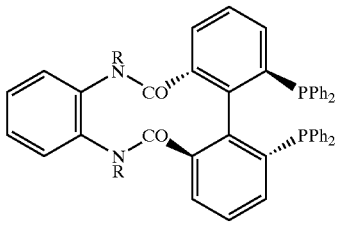
L44
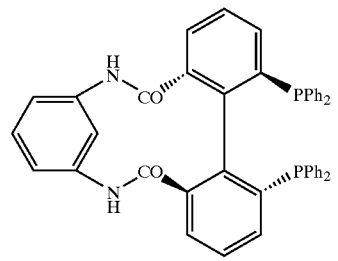
L45
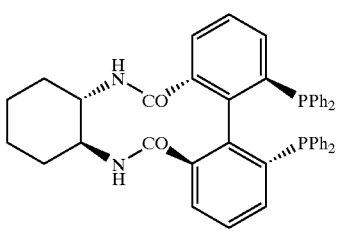
L46
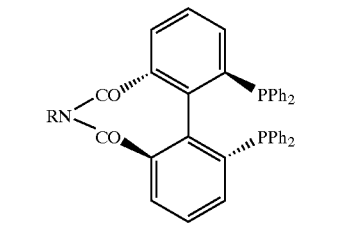
L47
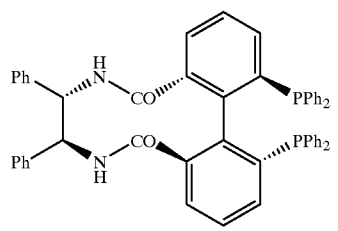
L48
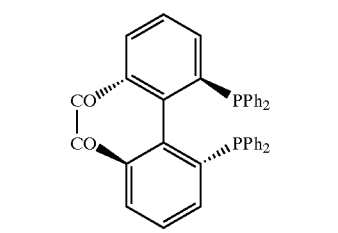

L49
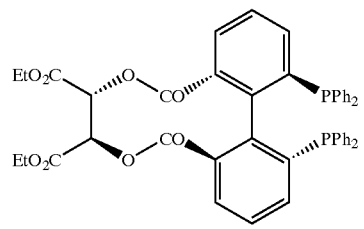
L50
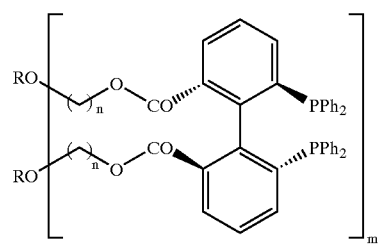
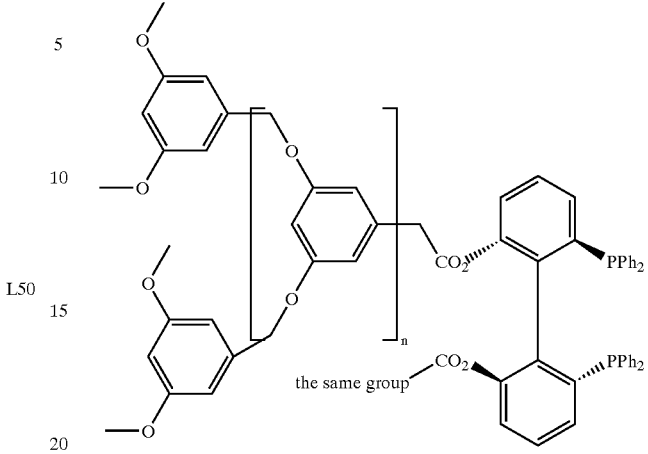
L54
L51
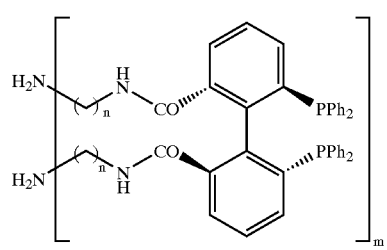
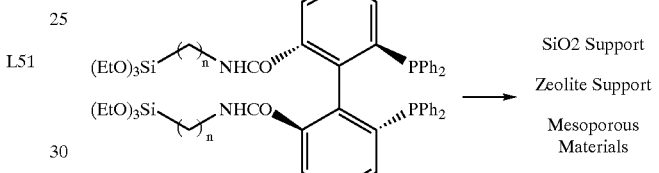
L55
L52
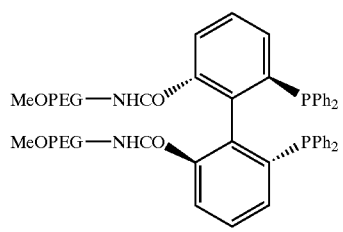
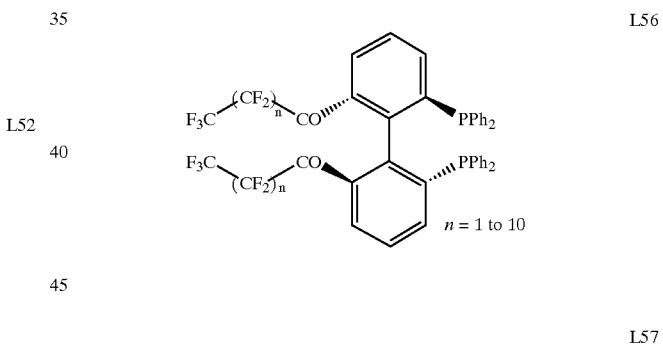
L56
L53
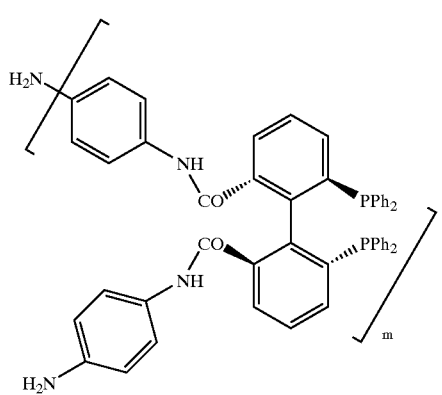
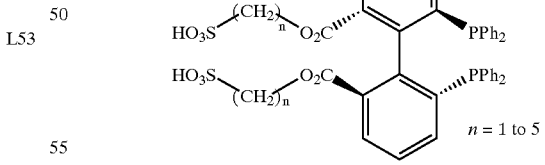
L57
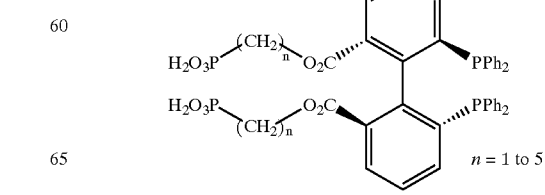
L58

L59
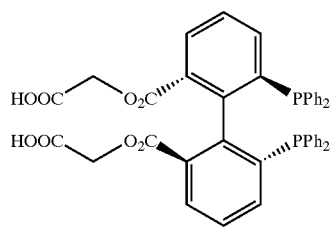
L60
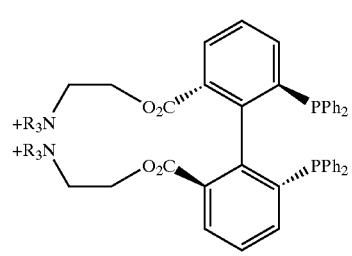
L61
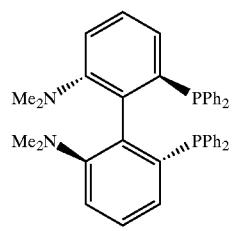
L62
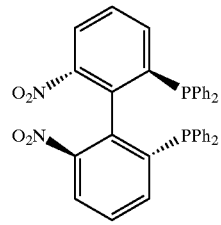
L63
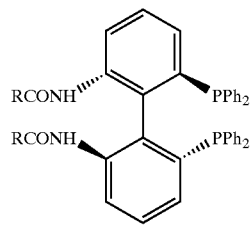
L64
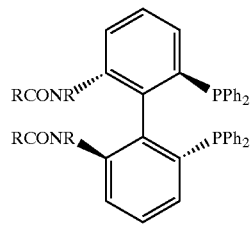
L65
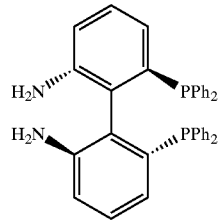
L66
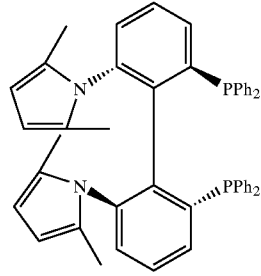
L67
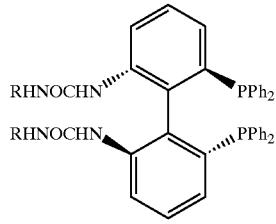
L68
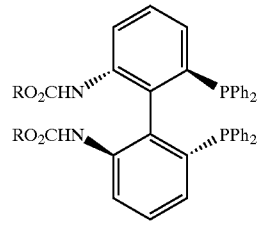
L69
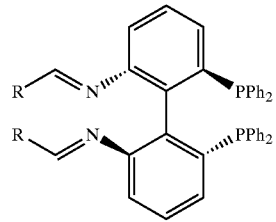
L70
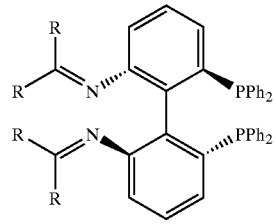

L71
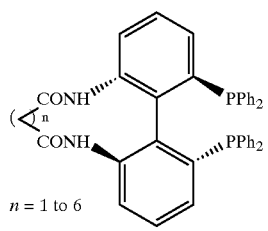
n = 1 to 6
L72
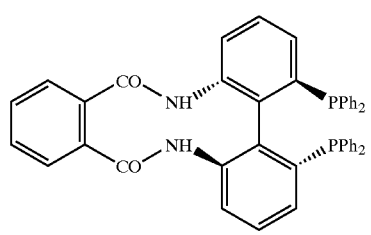
L73
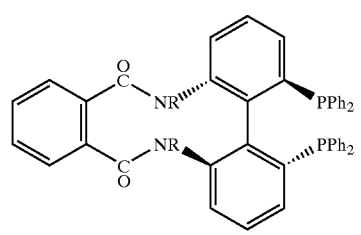
L74
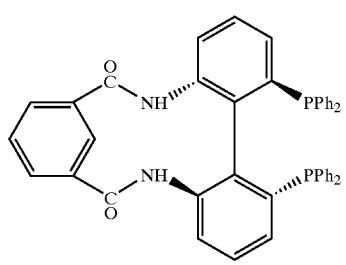
L75
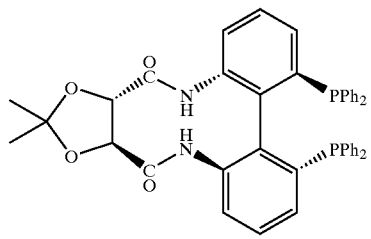
L76
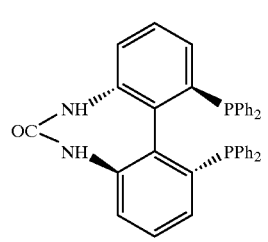
L77
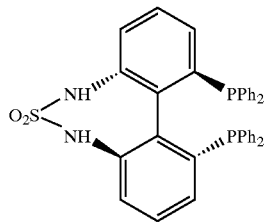
L78
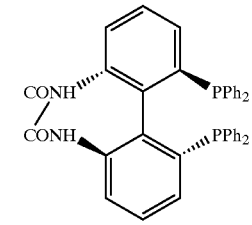
L79
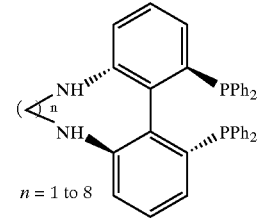
n = 1 to 8
L80
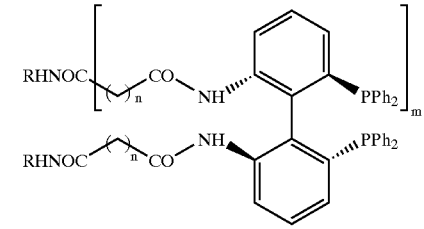
L81
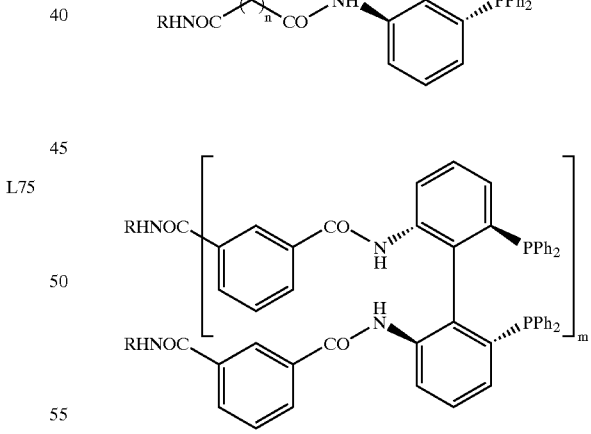
L82
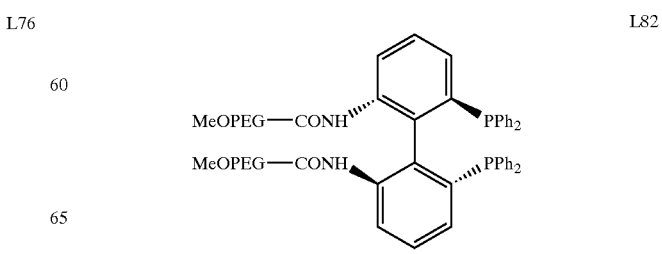

L83, L84, L85, L86, L87, L88, L89, L90, L91, L92, L93, L94

-continued

L95 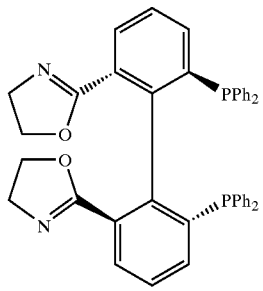

L96 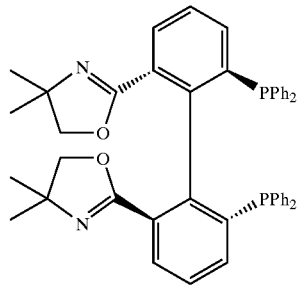

L97

L98

L99

L100

L101

L102

19. A catalyst prepared by a process comprising: contacting a transition metal salt, or a complex thereof, and a ligand according to claim 1.

20. The catalyst of claim 19, wherein said catalyst is a racemic mixture of enantiomers.

21. The catalyst of claim 19, wherein said catalyst is a non-racemic mixture of enantiomers.

22. The catalyst of claim 19, wherein said catalyst is one of the enantiomers.

23. The catalyst of claim 19, having an optical purity of at least 95% ee.

24. The catalyst of claim 19, wherein said transition metal is selected from the group consisting of: Pt, Pd, Rh, Ru, Ir, Cu, Ni, Mo, Ti V, Re and Mn.

25. The catalyst of claim 19, wherein said transition metal is selected from the group consisting of: Pd, Rh, Ru and Ir.

26. The catalyst of claim 24, wherein said transition metal salt, or complex thereof, is selected from the group consisting of: $PtCl_2$; $Pd_2(DBA)_3$; $Pd(OAc)_2$; $PdCl_2(RCN)_2$; (Pd (allyl)Cl)$_2$; $(Rh(COD)Cl)_2$; $(Rh(COD)_2)X$; $Rh(acac)(CO)_2$; $Rh(ethylene)_2(acac)$; $Rh(CO)_2Cl_2$; $Ru(RCOO)_2$ (diphosphine); Ru(methylallyl)2(diphosphine); Ru(aryl group)$X_2$(diphosphine); $RuCl_2(COD)$; $(Rh(COD)_2)X$; $RuX_2$(diphosphine); $RuCl_2(=CHR)(PR'_3)_2$; $Ru(ArH)Cl_2$; $Ru(COD)(methylallyl)_2$; $(Ir(COD)_2Cl)_2$; $(Ir(COD)_2)X$; Cu(OTf); $Cu(OTf)_2$; Cu(Ar)X; CuX; $NiX_2$; $Ni(COD)_2$; $MoO_2(acac)_2$; $Ti(OiPr)_4$; $VO(acac)_2$; $MeReO_3$; MnX2 and $Mn(acac)_2$; wherein each R and R' is independently selected from the group consisting of: alkyl or aryl; Ar is an aryl group; and X is a counteranion.

27. The catalyst of claim 26, wherein said counteranion X is selected from the group consisting of: halogen, $BF_4$, $B(Ar)_4$ wherein Ar is 3,5-di-trifluoromethyl-1-phenyl $ClO_4$, $SbF_6$, $CF_3SO_3$, RCOO and a mixture thereof.

28. The catalyst of claim 19, prepared in situ or as an isolated compound.

29. A process for preparation of an asymmetric compound comprising:
contacting a substrate capable of forming an asymmetric product by an asymmetric reaction and a catalyst prepared by a process comprising: contacting a transition metal salt, or a complex thereof, and a ligand according to claim 1.

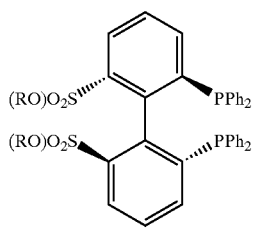
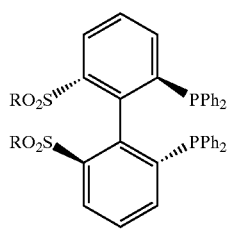
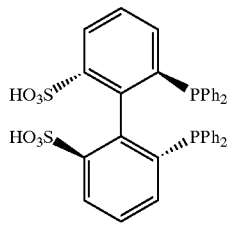
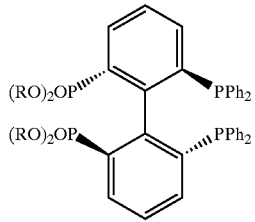
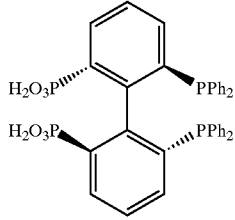
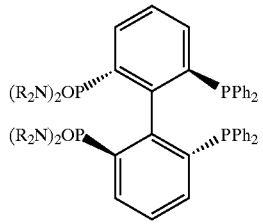

30. The process of claim 29, wherein said asymmetric reaction is selected from the group consisting of: hydrogenation, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation.

31. The process of claim 30, wherein said asymmetric reaction is hydrogenation; and said substrate is selected from the group consisting of ethylenically unsaturated compound, imine, ketone, enamine, enamide and vinyl ester.

32. The process of claim 31, wherein said catalyst is an Ru complex of chiral ligand selected from the group consisting of: C1-TunaPhos, C2-TunaPhos, C3-TunaPhos, C4-TunaPhos, C5-TunaPhos and C6-TunaPhos, and said asymmetric reaction is hydrogenation of ketones to produce a chiral alcohol.

* * * * *

UNITED STATES PATENT AND TRADEMARK OFFICE
CERTIFICATE OF CORRECTION

PATENT NO. : 6,521,769 B1
DATED : February 18, 2003
INVENTOR(S) : Zhang

It is certified that error appears in the above-identified patent and that said Letters Patent is hereby corrected as shown below:

<u>Column 1,</u>
Line 7, please insert the following:
-- STATEMENT OF GOVERNMENT RIGHTS
This invention was made with support from the Government under ONR Contract No. N000141-0733 and NIH Grant No. 1R01 GM5882-01A1. The Government has certain rights in the invention. --.

Signed and Sealed this

Twenty-second Day of November, 2005

JON W. DUDAS
*Director of the United States Patent and Trademark Office*

UNITED STATES PATENT AND TRADEMARK OFFICE
CERTIFICATE OF CORRECTION

PATENT NO. : 6,521,769 B1
DATED : February 18, 2003
INVENTOR(S) : Zhang

It is certified that error appears in the above-identified patent and that said Letters Patent is hereby corrected as shown below:

Column 1,
Line 7, insert the following:
-- STATEMENT OF GOVERNMENT RIGHTS
This invention was made with support from the Government under ONR Contract No. N000141-0733 and NIH Grant No. 1R01 GM5882-01A1. The Government has certain rights in the invention. --.

Signed and Sealed this

Seventh Day of February, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,521,769 B1 | Page 1 of 1 |
| APPLICATION NO. | : 09/665456 | |
| DATED | : February 18, 2003 | |
| INVENTOR(S) | : Zhang | |

It is certified that error appears in the above-identified patent and that said Letters Patent is hereby corrected as shown below:

<u>Column 1,</u>
Line 7, insert the following:
-- STATEMENT OF GOVERNMENT RIGHTS
This invention was made with support from the Government under ONR Contract No. N00014-96-1-0733 and NIH Grant No. 1R01 GM5882-01A1. The Government has certain rights in the invention. --.

This certificate supersedes the Certificate of Correction issued November 22, 2005 and February 7, 2006.

Signed and Sealed this

Twenty-second Day of July, 2008

JON W. DUDAS
*Director of the United States Patent and Trademark Office*

(12) EX PARTE REEXAMINATION CERTIFICATE (6217th)
United States Patent
Zhang

(10) Number: US 6,521,769 C1
(45) Certificate Issued: Apr. 29, 2008

(54) CHIRAL PHOSPHINES, TRANSITION METAL COMPLEXES THEREOF AND USES THEREOF IN ASYMMETRIC REACTIONS

(75) Inventor: Xumu Zhang, State College, PA (US)

(73) Assignee: The United States of America as represented by the Secretary of the Navy, Washington, DC (US)

Reexamination Request:
No. 90/007,906, Jan. 31, 2006

Reexamination Certificate for:
Patent No.: 6,521,769
Issued: Feb. 18, 2003
Appl. No.: 09/665,456
Filed: Sep. 19, 2000

Certificate of Correction issued Nov. 22, 2005.

Certificate of Correction issued Feb. 7, 2006.

Related U.S. Application Data
(60) Provisional application No. 60/154,845, filed on Sep. 20, 1999.

(51) Int. Cl.
*B01J 31/16* (2006.01)
*B01J 31/24* (2006.01)
*C07F 9/655* (2006.01)
*C07F 9/50* (2006.01)
*C07F 9/572* (2006.01)

(52) U.S. Cl. .......................... 556/19; 540/468; 540/542; 540/544; 540/547; 540/548; 549/12; 549/16; 549/17; 549/232; 549/349; 556/1; 556/136; 556/137; 556/405; 556/419; 556/45; 556/51; 556/479; 562/11; 562/55; 562/59; 562/67

(58) Field of Classification Search ...................... None
See application file for complete search history.

(56) References Cited
U.S. PATENT DOCUMENTS

| 5,481,008 | A | | 1/1996 | Broger et al. ............... 549/292 |
|---|---|---|---|---|
| 5,600,015 | A | | 2/1997 | Broger et al. ............... 568/396 |
| 5,621,128 | A | | 4/1997 | Jendralla ...................... 556/18 |
| 5,627,293 | A | | 5/1997 | Pugin ........................... 556/11 |
| 5,847,222 | A | | 12/1998 | Yokozawa et al. ............ 568/16 |
| 5,880,301 | A | | 3/1999 | Shibasaki et al. ............. 556/21 |
| 5,907,045 | A | | 5/1999 | Antognazza et al. ........... 549/6 |
| 5,990,318 | A | * | 11/1999 | Chan et al. ................. 548/412 |
| 6,162,951 | A | * | 12/2000 | Polywka et al. .............. 568/13 |
| 6,169,192 | B1 | * | 1/2001 | Pugin et al. .................. 556/11 |

FOREIGN PATENT DOCUMENTS

| EP | 1002801 | 5/2000 |
|---|---|---|
| EP | 1060793 | 5/2000 |

OTHER PUBLICATIONS

Greene TW and Wuts PGM. Protective Groups in Organic Synthesis. 1991, pp. 10–13 and 104–105.*

Zhang et al. "Synthesis of Chiral Bisphosphines with Tunable Bite Angles and Their Applications in Asymmetric Hydrogenation of β–Ketoesters". May 28, 2000. American Chemical Society, pp. 6223–6226.

* cited by examiner

*Primary Examiner*—Evelyn Mei Huang

(57) ABSTRACT

Chiral ligands and transition metal complexes based on such chiral ligands useful in asymmetric catalysis are disclosed. The chiral ligands include chiral C1–C6 TunaPhos ligands. The ruthenium TunaPhos complex reduces ketones to the corresponding alcohols with 95–99.6% enantioselectivity. The transition metal complexes of the chiral ligands are useful in asymmetric reactions such as asymmetric hydrogenation, hydride transfer, hydrosilylation, hydroboration, hydrovinylation, hydroformylation, hydrocarboxylation, isomerization, allylic alkylation, cyclopropanation, Diels-Alder reaction, Heck reaction, isomerization, Aldol reaction, Michael addition and epoxidation reactions.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–17 are cancelled.

Claims 18, 19 and 29 are determined to be patentable as amended.

Claims 20–28 and 30–32, dependent on an amended claim, are determined to be patentable.

18. A ligand selected from the group consisting of:

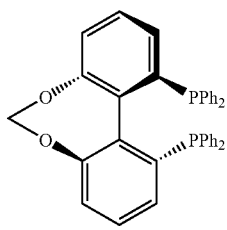
L1

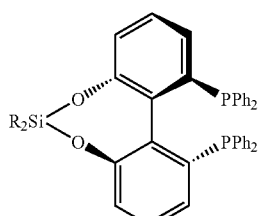
L2

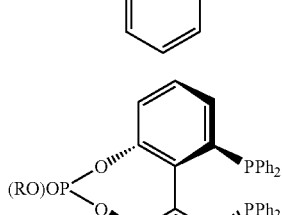
L3

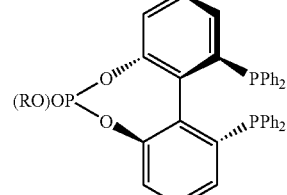
L4

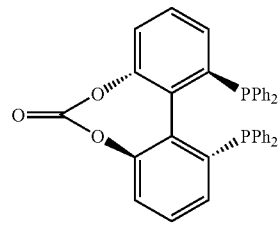
L5

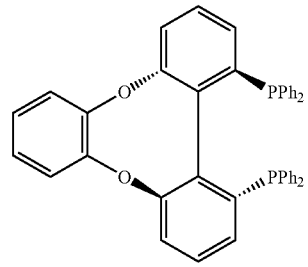
L6

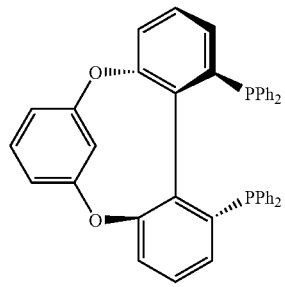
L7

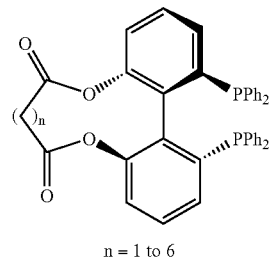
L8 n = 1 to 6

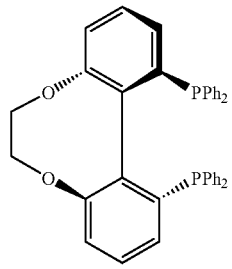
L9

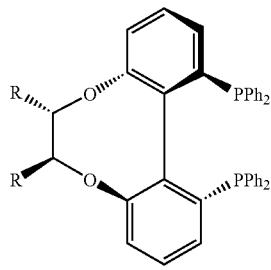
L10

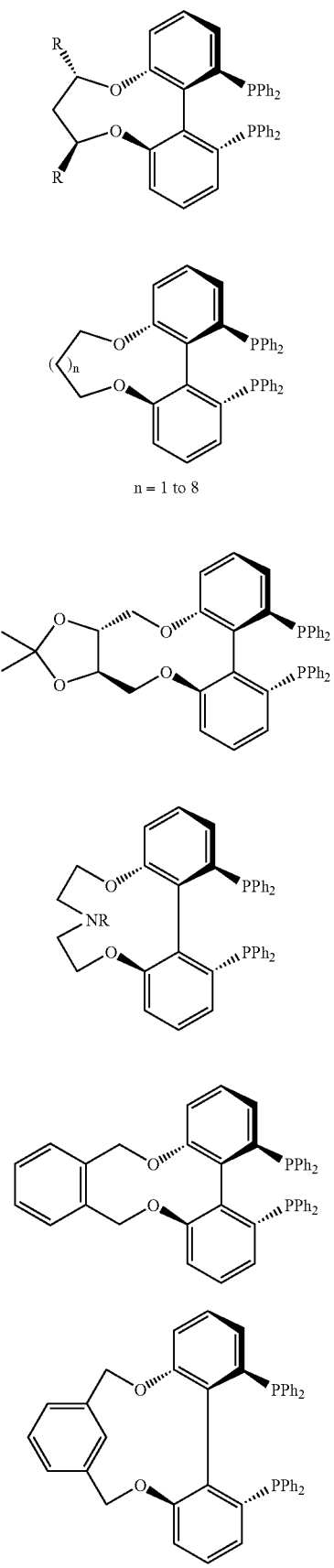

L23
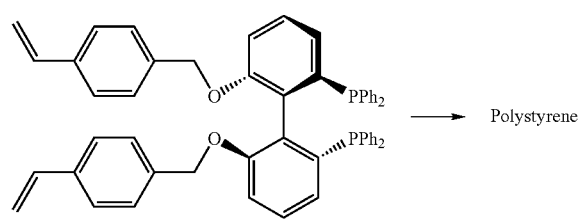 → Polystyrene
L24
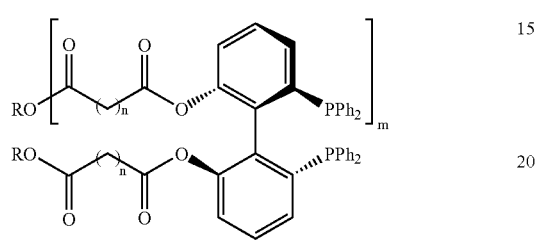
L25
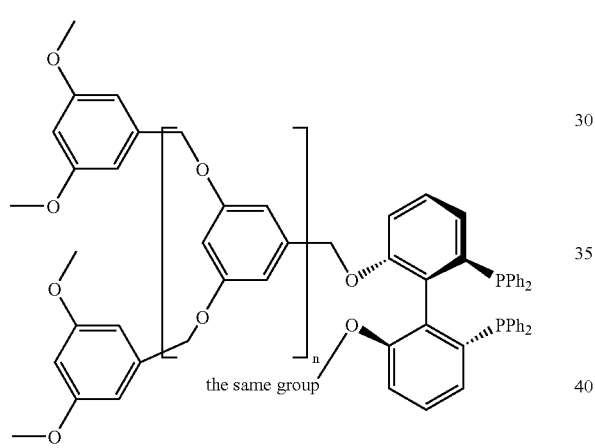
L26
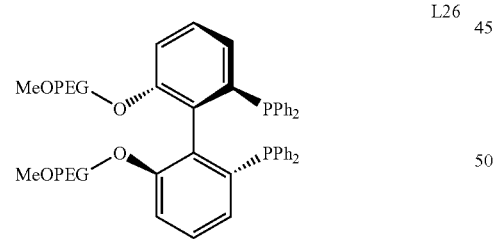
L27
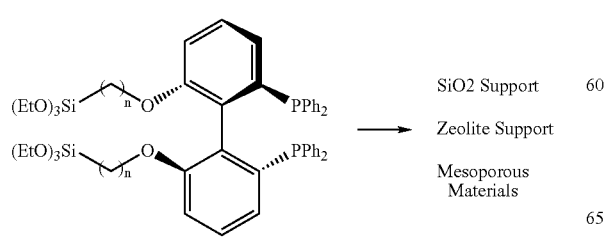 → SiO2 Support
Zeolite Support
Mesoporous Materials
L28
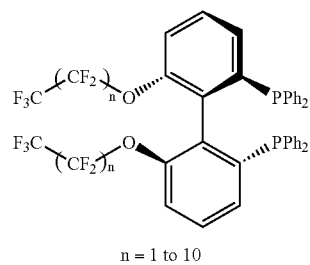
n = 1 to 10
L29
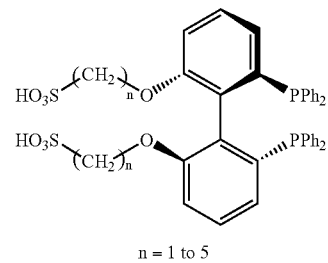
n = 1 to 5
L30
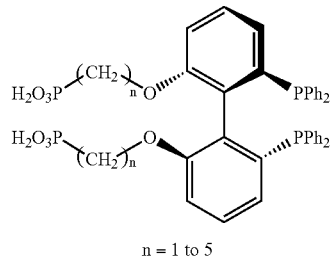
n = 1 to 5
L31
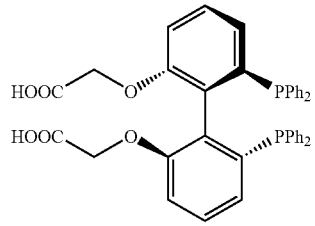
L32
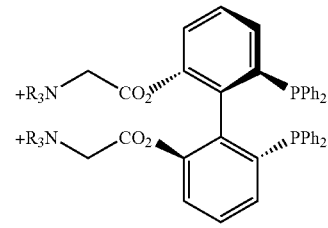
L33
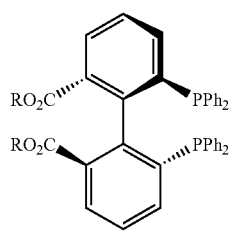

-continued
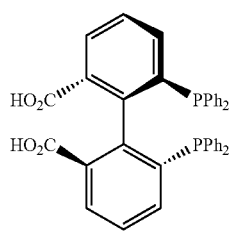 L34
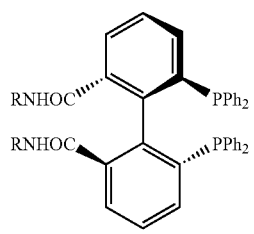 L35
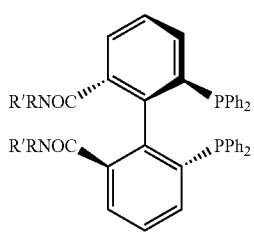 L36
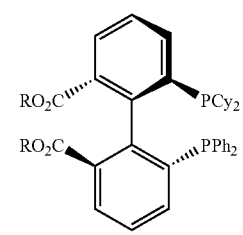 L37
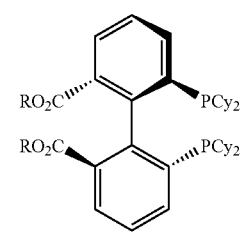 L38
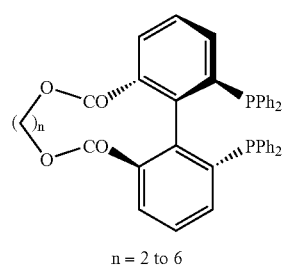 L39
n = 2 to 6
-continued
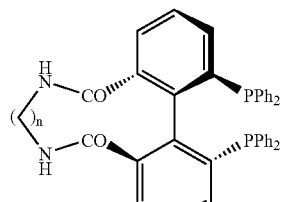 L40
n = 2 to 6
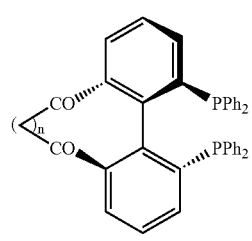 L41
n = 1 to 6
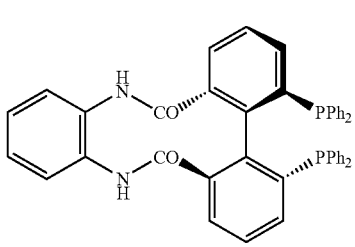 L42
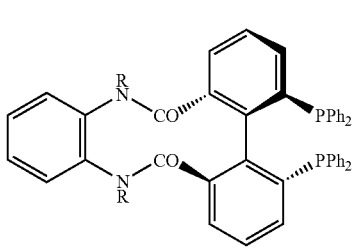 L43
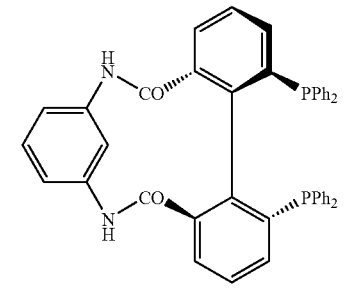 L44
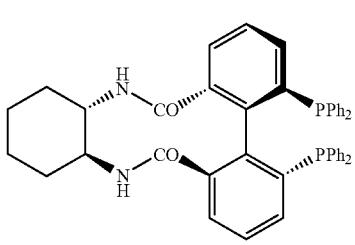 L45

-continued
L46
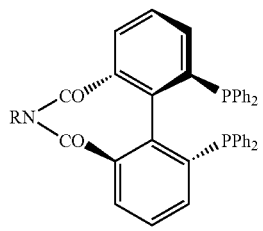
L47
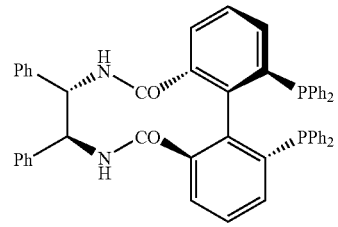
L48
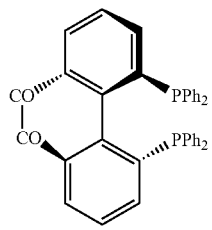
L49
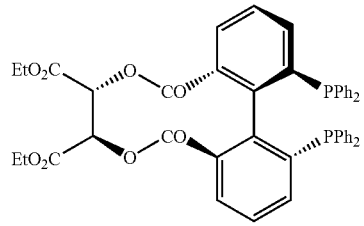
L50
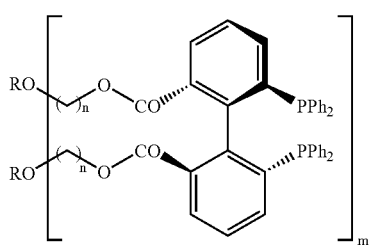
L51
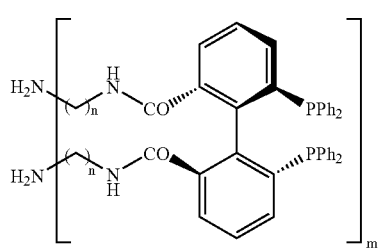
-continued
L52
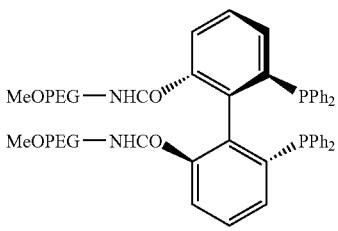
L53
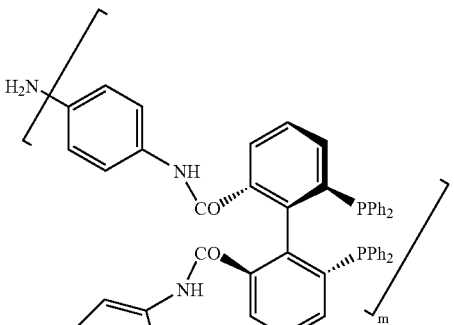
L54
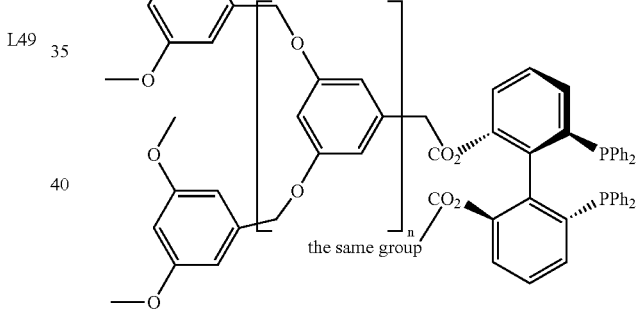
the same group
L55
(EtOH)₃Si... → SiO2 Support, Zeolite Support, Mesoporous Materials
n = 2 to 8
L56
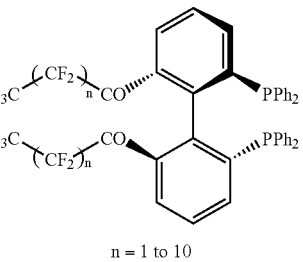
n = 1 to 10

-continued
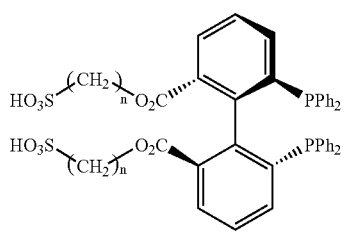
n = 1 to 5
L57
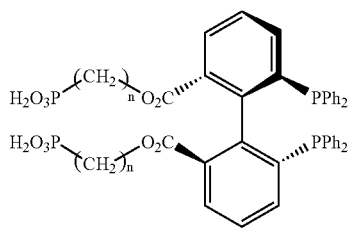
n = 1 to 5
L58
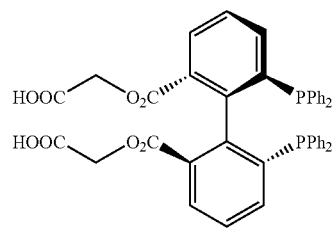
L59
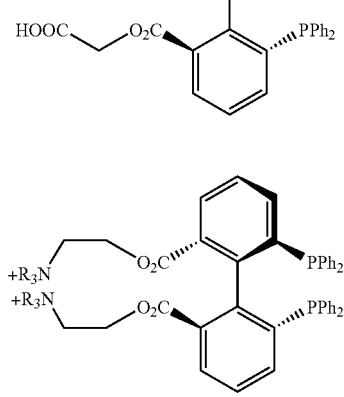
L60
[
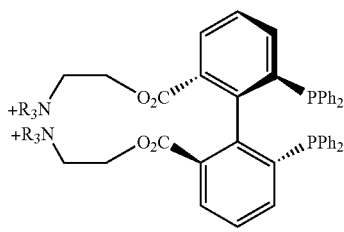
]
L61
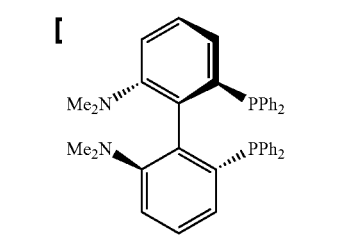
L62
-continued
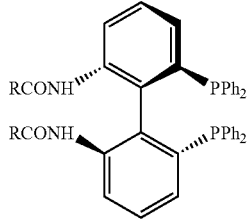
L63
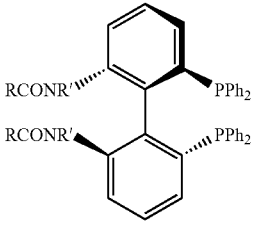
L64
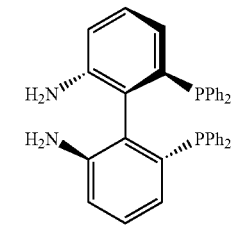
L65
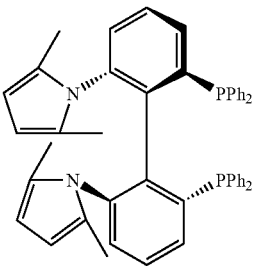
L66
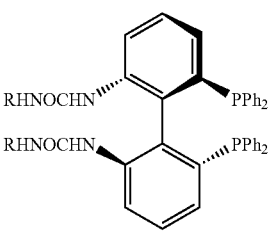
L67
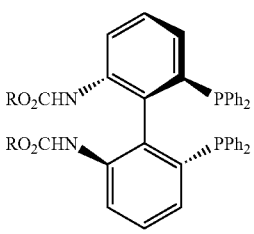
L68
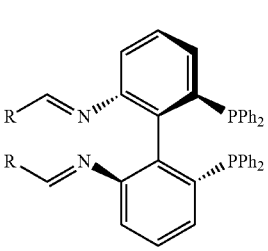
L69

-continued
L70
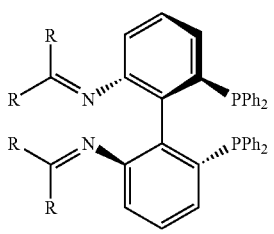
L71
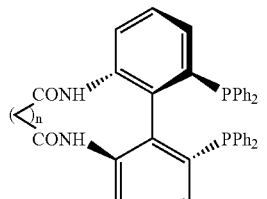
n = 1 to 6
L72
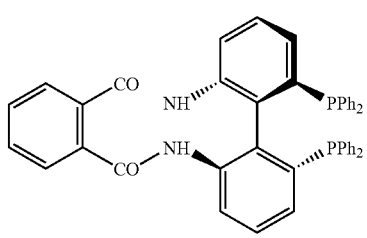
L73
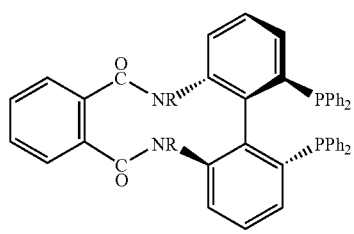
L74
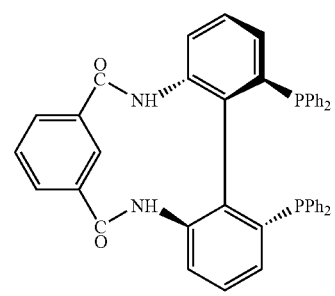
L75
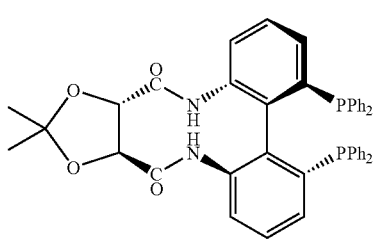
-continued
L76
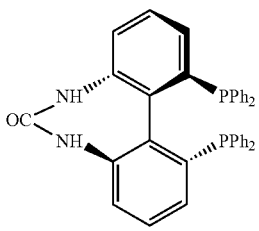
L77
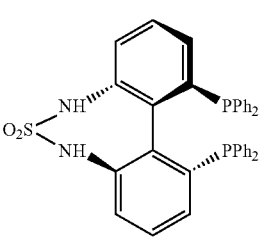
L78
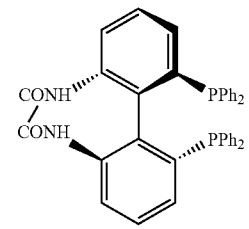
L79
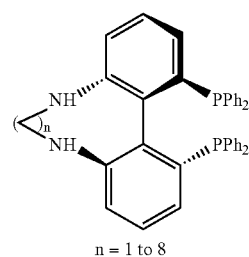
n = 1 to 8
L80
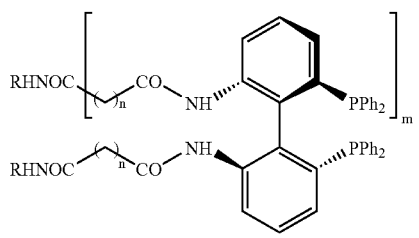
L81
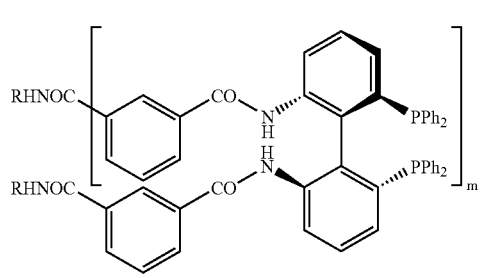

-continued
L82
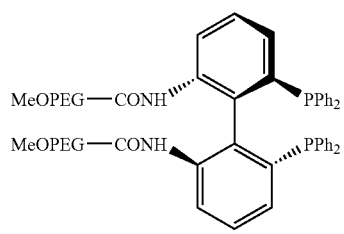
L83
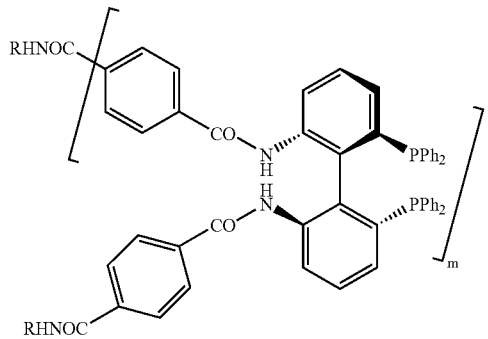
L84
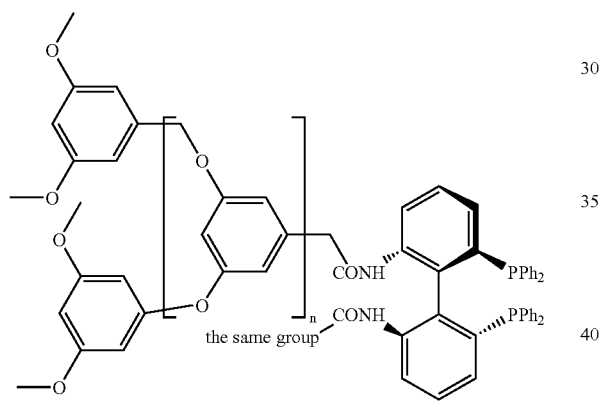
L85
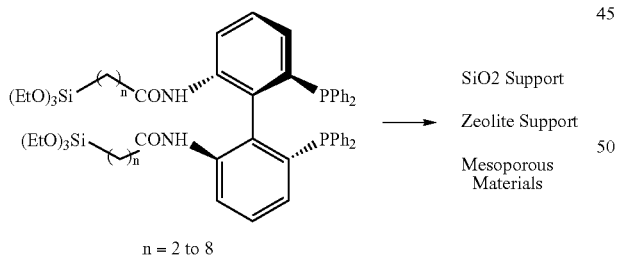
→ SiO2 Support
Zeolite Support
Mesoporous Materials
n = 2 to 8
L86
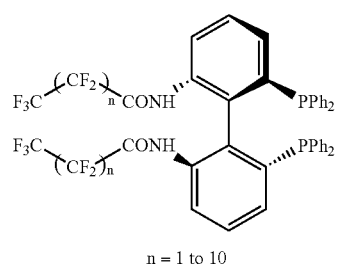
n = 1 to 10
-continued
L87
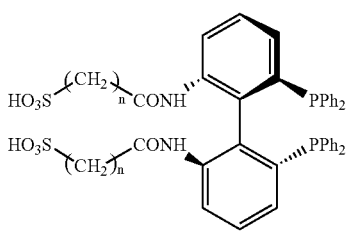
n = 1 to 5
L88
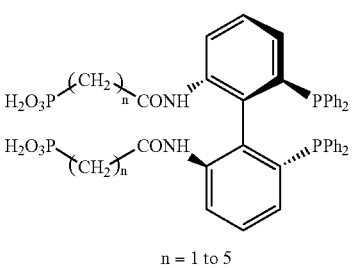
n = 1 to 5
L89
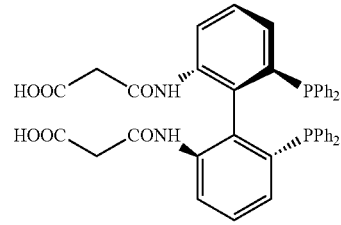
L90
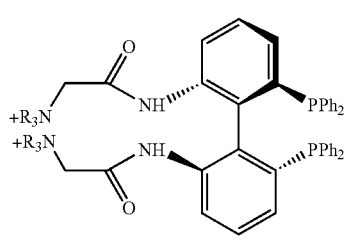
L91
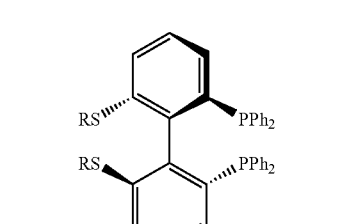
L92
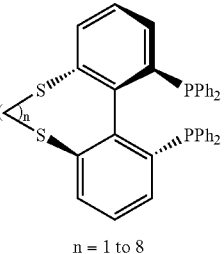
n = 1 to 8

-continued

L93 L94 L95 L96 L97 L98

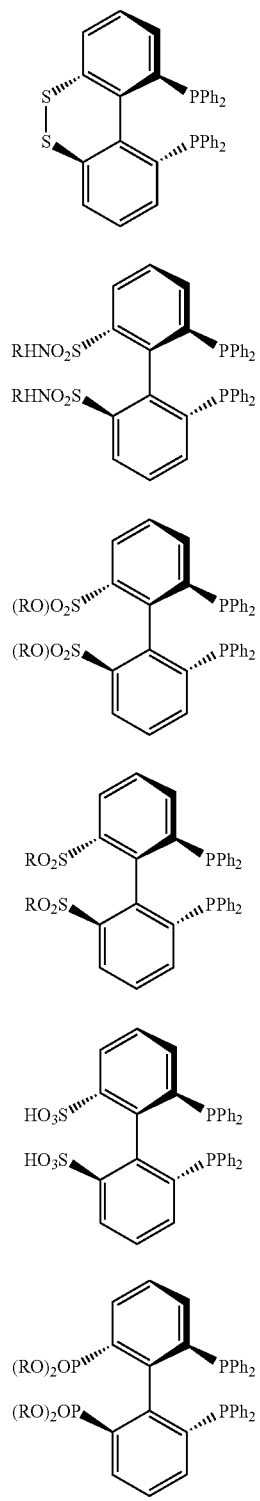

-continued

L99 L100 L101 L102

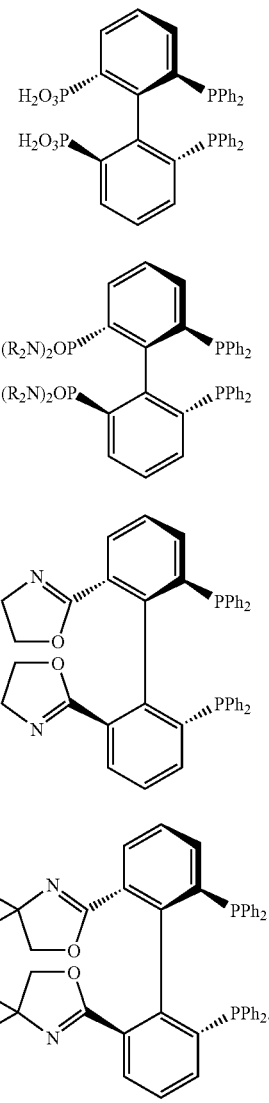

19. A catalyst prepared by a process comprising:

contacting a transition metal salt, or a complex thereof, and a ligand according to claim [1] *18*.

29. A process for preparation of an asymmetric compound comprising:

contacting a substrate capable of forming an asymmetric product by an asymmetric reaction and a catalyst prepared by a process comprising:

contacting a transition metal salt, or a complex thereof, and a ligand according to claim [1] *18*.

* * * * *